(12) United States Patent
Shen et al.

(10) Patent No.: US 10,829,730 B2
(45) Date of Patent: Nov. 10, 2020

(54) MICRODEVICE PLATFORM RECAPITULATING HYPOXIC TISSUE MICROENVIRONMENTS

(71) Applicant: UNIVERSITY OF SOUTHERN CALIFORNIA, Los Angeles, CA (US)

(72) Inventors: Keyue Shen, Los Angeles, CA (US); Yuta Ando, Los Angeles, CA (US); Daniel Yen, Los Angeles, CA (US); Hoang Ta, Los Angeles, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 163 days.

(21) Appl. No.: 15/941,374

(22) Filed: Mar. 30, 2018

(65) Prior Publication Data

US 2018/0291330 A1   Oct. 11, 2018

Related U.S. Application Data

(60) Provisional application No. 62/478,810, filed on Mar. 30, 2017.

(51) Int. Cl.
*C12M 3/00* (2006.01)
*C12M 1/00* (2006.01)
(Continued)

(52) U.S. Cl.
CPC .............. *C12M 41/34* (2013.01); *C12M 3/04* (2013.01); *C12M 23/16* (2013.01); *C12M 25/02* (2013.01); *C12N 5/0693* (2013.01)

(58) Field of Classification Search
CPC ....... C12M 41/30; C12M 41/32; C12M 41/34
See application file for complete search history.

(56) References Cited

U.S. PATENT DOCUMENTS

| 5,302,515 A * | 4/1994 | Goodwin, Jr. ........ B01L 3/5027 422/421 |
| 2003/0003570 A1 * | 1/2003 | Kanegasaki ...... B01L 3/502715 435/288.5 |

(Continued)

*Primary Examiner* — Nathan A Bowers
(74) *Attorney, Agent, or Firm* — Brooks Kushman P.C.

(57) ABSTRACT

Hypoxia plays a central role in cancer progression and resistance to therapy. A microdevice platform is engineered to recapitulate the intratumor oxygen gradients that drive the heterogeneous hypoxic landscapes in solid tumors. The microdevice design features a "tumor section"-like culture by incorporating a cell layer between two diffusion barriers, where an oxygen gradient is established by cellular metabolism and physical constraints. The oxygen gradient is confirmed by numerical simulation and imaging-based oxygen sensor measurement. Spatially-resolved hypoxic signaling in cancer cells is also demonstrated through immunostaining, gene expression assay, and hypoxia-targeted drug treatment. The microdevice platform can accurately generate and control oxygen gradients, eliminates complex microfluidic handling, allows for incorporation of additional tumor components, and is compatible with high-content imaging and high-throughput applications. It is well suited for understanding hypoxia-mediated mechanisms in cancer disease and other biological tissues and processes, and discovery of new therapeutics.

26 Claims, 18 Drawing Sheets

(51) Int. Cl.
*C12M 1/34* (2006.01)
*C12M 3/06* (2006.01)
*C12M 3/04* (2006.01)
*C12M 1/12* (2006.01)
*C12N 5/09* (2010.01)

(56) References Cited

U.S. PATENT DOCUMENTS

| 2016/0178618 A1* | 6/2016 | Freyer | C12M 25/14 |
| | | | 435/7.1 |
| 2016/0340631 A1* | 11/2016 | Wang | C12M 23/16 |
| 2018/0346867 A1* | 12/2018 | Oliver | C12M 23/16 |

* cited by examiner

Hypoxyprobe™-1 immunostaining (24-hour)

MICRODEVICE PLATFORM RECAPITULATING HYPOXIC TISSUE MICROENVIRONMENTS

CROSS-REFERENCE TO RELATED APPLICATIONS

This application claims the benefit of U.S. provisional application Ser. No. 62/478,810 filed Mar. 30, 2017, the disclosure of which is hereby incorporated in its entirety by reference herein.

TECHNICAL FIELD

In at least one aspect, the present invention is related to devices that simulate hypoxia as observed in various tumor cells and stem cell niches.

BACKGROUND

Cancer remains one of the leading causes of death despite the vast investment and efforts in research and drug development. Over 1.68 million new cancer cases and 0.6 million cancer deaths are projected to occur in the United States alone in 2017[1]. Resistance towards conventional chemo- and radio-therapies as well as the fast-growing immuno-therapies presents a significant challenge in cancer treatments, particularly in solid tumors[2,3]. The tumor microenvironment (TME) consists of complex cellular and molecular interactions that regulate the progression and therapeutic response of tumors[4]. Hypoxia, the condition of oxygen deficiency, is a central player in the TME and cancer progression[5,6]. Notably, degrees of hypoxia in solid tumors are very heterogeneous and can range from 0.5-2% oxygen saturation compared to 4-7% in healthy tissues and 21% in atmospheric air[7,8]. Different degrees of hypoxia induce varying levels of metabolic adaptation, extracellular matrix (ECM) remodeling, epithelial-mesenchymal transition (EMT), angiogenesis, pH regulation, and immune suppression[9,10]. It also promotes cancer stem-like cell (CSC) phenotypes, adding to tumor heterogeneity and therapy resistance[11]. Recapitulating in vivo hypoxic conditions will therefore facilitate the screening and development of new therapeutics[12].

Considerable efforts have been made to establish hypoxic tumor models that can be analyzed with ease and reproducibility. In vivo models provide naturally formed[13] or induced[14] hypoxia. However, these models typically involve significant individual variabilities, high cost, and low throughput[15-17]. They also have limited spatiotemporal and cellular resolutions inherent to most in vivo imaging modalities[17]. In vitro models can provide a high level of manipulation, specificity, sensitivity, and reproducibility that are difficult to obtain in vivo[16]. Hypoxia can be induced in vitro using chemical methods[18], hypoxia chambers[19], spheroid cultures[20], and micro-engineering approaches[21]. Chemical induction of hypoxia can adversely affect signaling pathways other than those regulated by hypoxia[18]. Commercially available hypoxia chambers provide one oxygen concentration at a time, thus limiting its throughput in testing cell responses to different oxygen levels. Moreover, these approaches fail to capture the spatial complexity of oxygen profiles and the resulted crosstalk in a hypoxic tumor[22,23]. Tumor spheroid cultures can induce a hypoxic gradient that histologically resemble avascular tumor nests[24]. However, spheroids are generally incompatible with high-content analysis such as live-cell tracking and spatiotemporally resolved single-cell analysis, which would otherwise require laborious post-processing such as embedding and sectioning, or expensive, deep imaging platforms[25,26]. Engineered 3-dimensional (3D) cultures have also emerged as an alternative method to capture gradients of oxygen and nutrients. For instance, paper-supported 3D cell cultures have been developed to recapitulate gradients in spheroids and tumors, where layers of 2D cultures are stacked to establish the gradients, and disassembled for imaging and analysis[27]. Such methods lack a lateral gradient profile for microscopy, and require additional handling to analyze cells on each layer. Microfluidic platforms have been established to create oxygen gradients on a lateral surface to facilitate microscopic observation[28-32]. However, they often face challenges of high oxygen permeability of fabrication materials, maintenance of an accurate gradient, complicated fabrication processes, and microfluidic design/handling that are challenging to biological research laboratories. Those designs with continuous flow over the cells also prohibits lateral cell-cell communications between gradient zones through soluble mediators[33]. To date, there has not been a user-friendly, scalable in vitro hypoxic model that mimics the in vivo oxygen gradient and is compatible with high-content imaging and high-throughput applications.

Accordingly, there is need for a biomimetic cancer culture platform that is easy to handle and can be reproducibly analyzed.

SUMMARY

In at least one aspect, a novel approach to recapitulate a hypoxic gradient within a micropatterned monolayer culture of human cells, and in particular cancer cells is provided. Cellular metabolism is combined with micro-milled oxygen diffusion barriers to establish a natural hypoxic gradient. Induction of hypoxia in a microdevice is driven by cellular oxygen consumption, similar to the formation of tumor hypoxia due to increased oxygen demand by uncontrollably proliferating cells; therefore, the microdevice is able to mimic natural hypoxia induction while eliminating the need for an external source of oxygen control. The platform is integrated with oxygen sensors for real-time, spatially-resolved measurements and is compatible with microscopy-based techniques. It enables high-content, spatially-resolved analyses of cell phenotypic and gene expressions, and further allows for assessment of hypoxia-targeted drugs, as demonstrated below using tirapazamine (TPZ). Advantageously, the device and platform are a versatile tool for gaining insights into cancer biology and accelerate the development and discovery of new therapeutics.

In another aspect, the present invention provides a novel approach for recapitulating a hypoxic gradient within a micropatterned design of human tissue cells, and in particular cancer cells, referred to as 2D spheroids. These 2D spheroids were set into a microdevice, in which an oxygen concentration gradient is induced independently. With this biomimetic tissue (e.g., tumor) model, rapid insight into cancer biology can be achieved while reducing the high failure rate in the development of new anticancer drugs. In addition, the capacity for the chip to incorporate a patient's own cancer, stromal, and immune cells can revolutionize personalized, precision medicine for cancer therapies.

In another aspect, a device for inducing an oxygen concentration gradient is provided. The device includes a first component that is a diffusion barrier having a first space-defining surface, a second component having a second space-defining surface, and a layer of living cells disposed over the second space-defining surface. The first component is positioned proximate to the second component such that the first space-defining surface and the second space-defining surface define a confined space. An aqueous solution having dissolved oxygen therein fills the confined space. Characteristically, the first space-defining surface and the second space-defining surface are sufficiently close that passive oxygen diffusion in the confined space is insufficient to replenish oxygen consumed by cells thereby establishing an oxygen gradient in the confined space.

In another aspect, a device for inducing an oxygen concentration gradient is provided. The device includes a first component that is a diffusion barrier having a first space-defining surface; and a second component having a second space-defining surface. The first component is positioned proximate to the second component such that the first space-defining surface and the second space-defining surface define a confined space. Characteristically, the confined space defines a gap distance that is sufficiently small to inducing an oxygen concentration gradient when a layer of living cells in aqueous medium is disposed in the confined space.

In another aspect, an integrated system that combines microfluidic channels with the devices for inducing oxygen concentration gradients set forth herein. Advantageously, the microfluidics channel provides materials to the layer of living cells.

DETAILED DESCRIPTION

Figure 1A:
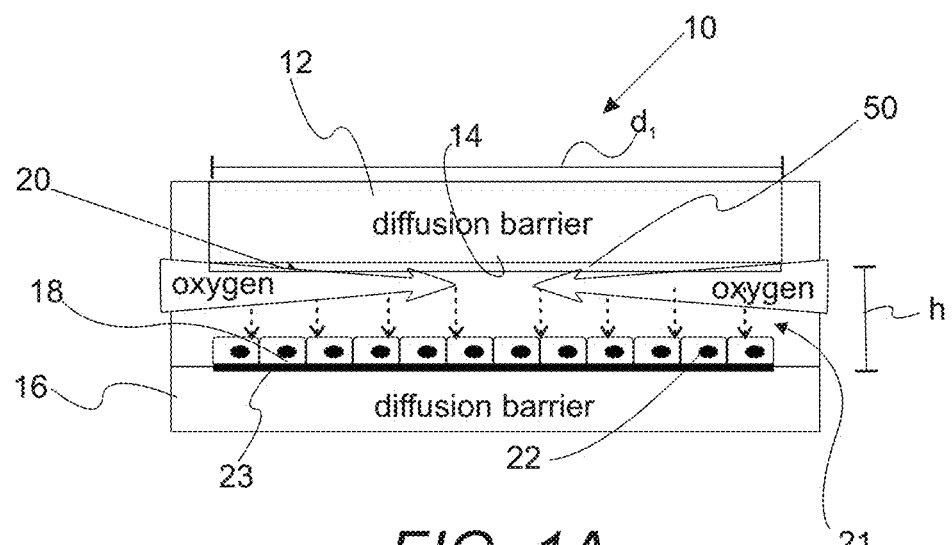
FIGS. 1A-1E. Recapitulation of a gradient of oxygen in a hypoxic microdevice. (A) Illustration of the working principle. Differential levels of oxygen across a cell monolayer are achieved with the addition of a physical barrier immediately above it. Cells are exposed to varying degrees of oxygen owing to the limited passive diffusion of oxygen in confined spaces, further enhanced by the cells' innate ability to consume oxygen. (B) Side view of the microdevice capable of inducing hypoxia. Computer-aided designs of the (C) cap and (D) base structures. (E) Assembled microdevice after micro-milling.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of" where one of these three terms is used herein, the presently disclosed and claimed subject matter can include the use of either of the other two terms.

Throughout this application, where publications are referenced, the disclosures of these publications in their entireties are hereby incorporated by reference into this application to more fully describe the state of the art to which this invention pertains.

Abbreviations

"CNC" means computer numerical control.
"ECM" means extracellular matrix.
"LCM" means laser capture microdissection.
"PC" means pillar center.
"PDMS" means polydimethylsiloxane.
"PE" means pillar edge.
"TPZ" means tirapazamine.

In an embodiment of the present invention, a device for inducing an oxygen concentration gradient (e.g., a gradient of hypoxia) is provided. With reference to FIGS. 1A-E, schematic illustrations of the oxygen concentration gradient-inducing device are provided. Device 10 includes first component 12 that is a diffusion barrier having a first space-defining surface 14. Device 10 also includes second component 16 which has second space-defining surface 18. Characteristically, first component 12 is positioned proximate to the second component 16 such that the first space-defining surface 14 and the second space-defining surface 18 define a confined space 20. In a refinement, the confined space is open along a periphery 21. The gap distance h between first space-defining surface 14 and second space-defining surface 18 is typically from about 30 μm to about 1000 μm. In a refinement, the gap distance h is from about 50 μm to about 500 μm. A first space-defining surface 14 has a smaller area than the area of second space-defining surface 18. When this is the case, first space-defining surface 14 will define the region that has the oxygen concentration gradient. In this regard, first space-defining surface 14 has an area from about 1 mm$^2$ to about 25 mm$^2$. In a variation, first space-defining surface 14 has an area from about 3 mm$^2$ to about 15 mm$^2$. In some variations, first space-defining surface 14 is substantially circular (e.g., disk-like). In these variations, first space-defining surface 14 can have a radius from about 0.5 mm to about 5 mm. In a refinement, first space-defining surface 14 has a radius from about 1 mm to about 3 mm.

Figure 2A:
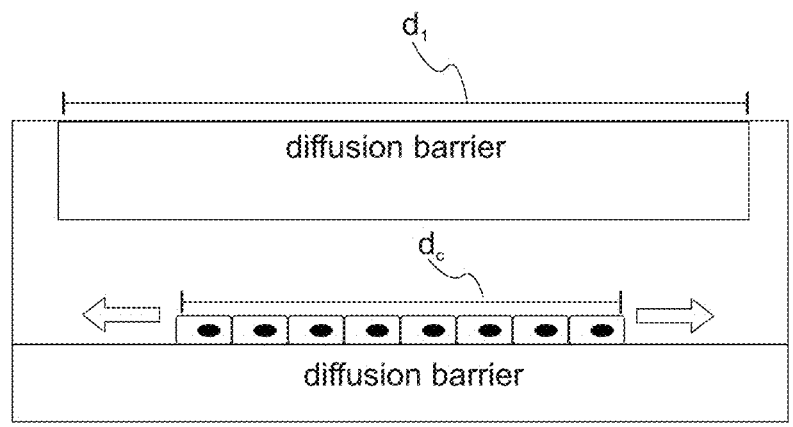
FIG. 2A. Device variation in which the cell island with smaller diameter than diffusion barrier can mimic growth of tumor under more physiological or pathophysiological level of oxygen concentrations in tumors.
Figure 2B:
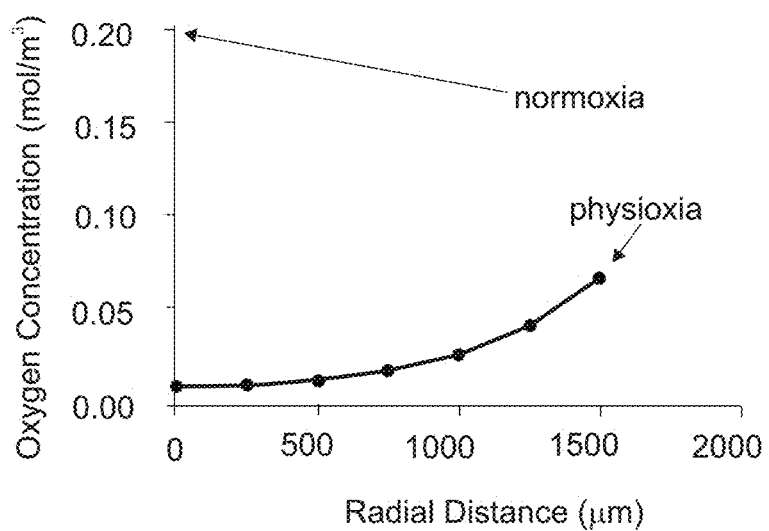
FIG. 2B: Plot of oxygen concentration versus radial distance for the variation of FIG. 3A.

Layer of living cells 22 is disposed over the second space-defining surface 18. In a refinement, the layer of living cells 22 is patterned onto second space-defining surface 18. In some refinements, the layer of living cells includes stem cells, normal cells and/or cancer cells (e.g., breast cancer cells). In other variations, the layer of living cells can include cells selected from the group consisting of cancer cells, stem cells, cardiomyocytes, neurons, hepatocytes, pancreatic cells, fibroblasts, immune cells, epithelial cells, endothelial cells, and combinations thereof. For example, cardiomyocytes can be used in the device to investigate ischemic heart disease. In a variation, an adhesion layer 23 (e.g., collagen or another ECM material) can be used to assist in adhering living cells 22 to second space-defining surface 18. It should be appreciated that layer of living cells 22 can have a smaller spatial extent (e.g., length or diameter) than the spatial extent $d_1$ of first space-defining surface 14. In this regard, $d_1$ is the largest distance which the living cells extend over second space-defining surface 18. Typically, this $d_1$ can be 1 to 20 mm. Alternatively, layer of living cells 22 has an area that is smaller than the area of first space-defining surface 14 set forth above. FIG. 2A illustrates the variation in which the cell layer has a smaller diameter $d_c$ than the diffusion barrier's diameter $d_1$. FIG. 2B shows that layer of cells with smaller diameter than diffusion barrier can mimic growth of tumor under more physiological or pathophysiological level of oxygen concentrations in tumors. In other variations, layer of living cells 22 can have a larger or equal spatial extent to that of first space-defining surface 14. Aqueous solution 24 fills the confined space 20. The aqueous solution typically has dissolved oxygen there. In a refinement, aqueous solution 24 is a cell culture medium. Characteristically, first space-defining surface 14 and second space-defining surface 18 are sufficiently close that passive oxygen diffusion in the confined space is insufficient to replenish oxygen consumed by cells thereby establishing an oxygen gradient in the confined space.

In a variation, first component 12 and second component 16 are each independently an oxygen diffusion barrier. Therefore, each of these components are typically formed from a material having an oxygen permeability of less than about 1×10$^{-7}$ cm$^3$/(cm$^2$-sec-atm)) at 25° C. and 1 atm. Examples of suitable materials include, but are not limited to, glass, metals, ceramics, polymers, and combinations thereof. In some applications thermoplastic polymers can be used. Specific polymers that are useful include poly(chloroprene), poly(isobutene-coisonrene), poly(vinyl chloride), poly(tetrafluoroethylene), low density poly(ethylene), high density poly(ethylene), poly(propylene), poly(vinylidene chloride), poly(trifluoro chloroethylene), poly(ethyl methacrylate), polycarbonate, poly(ethylene terephthalate), and combinations thereof. If transparency is needed, polycarbonate is a particularly useful material. In a refinement, first component 12 includes polycarbonate and second component 16 includes polyoxymethylene.

Figure 1B:
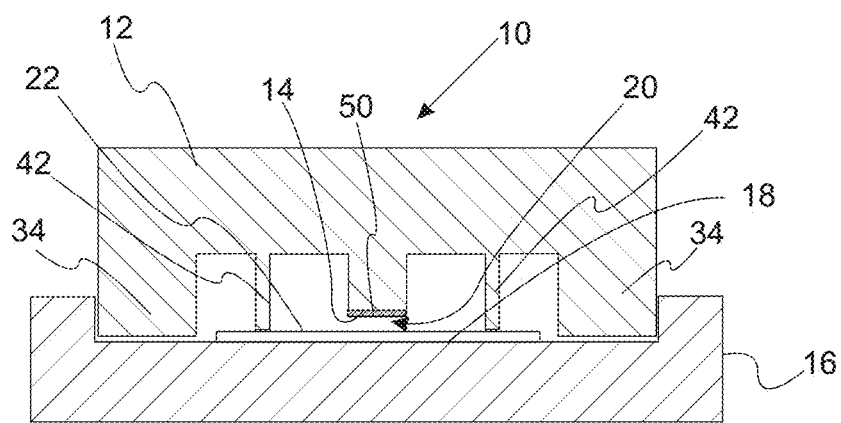
Figure 1C:
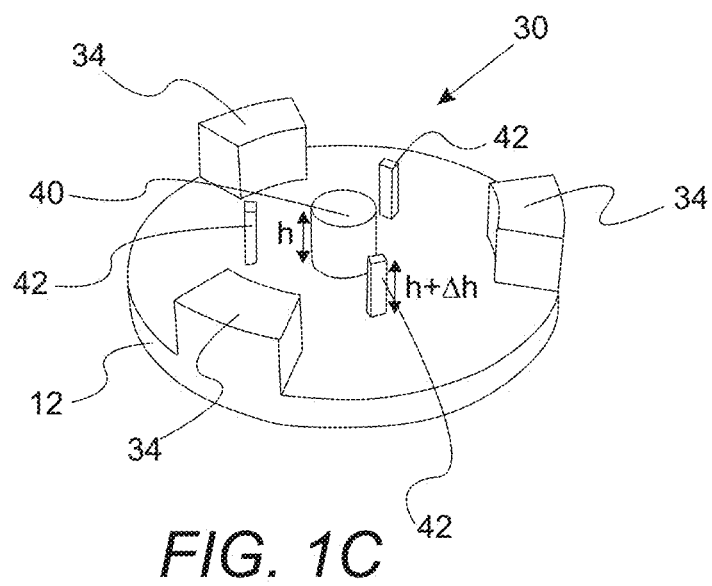
Figure 1D:
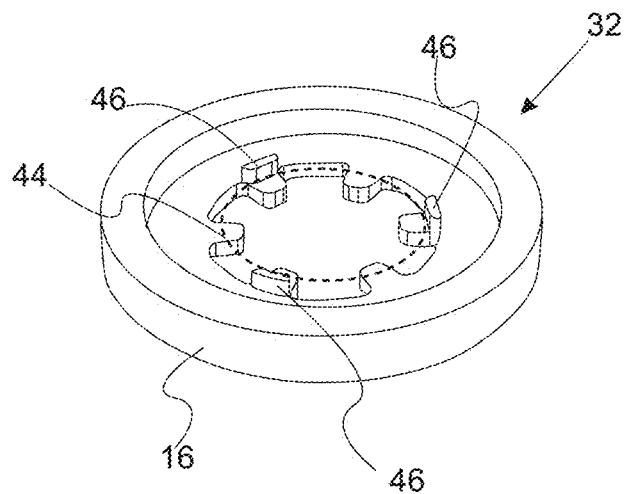

With reference to FIGS. 1B-E, schematic illustrations of and oxygen concentration gradient-inducing device formed from a cap structure and a base structure is provided. Device 10 includes cap structure 30 which mates to base structure 32 with a pillar defining the diffusion barrier. As depicted in FIGS. 1B and 1C, first component 12 is a cap structure with a central oxygen barrier pillar 40 and spatial reference pillars 42 that are longer than the central oxygen barrier pillar thereby defining a gap size h between the layer of living cells and the central oxygen barrier pillar. In this regard, the spatial reference pillars establish and maintain the gap distance h. Cap structure 30 also includes additional columns 34 that align to base structure 32. As depicted in FIGS. 1B and 1D, the second component 16 is a base structure with glass plate 44 (e.g., a 12 mm coverslip) being held by the base structure. Significantly, the plurality of living cells is disposed over the glass plate 34. In a refinement, the base structure includes three pegs 46 that snugly immobilize glass plate 14. In its assembled form, the reference pillars directly contact glass plate 44, providing precise spatial control over the desired gap size (FIG. 1 E).

Still referring to FIGS. 1A-E, device 10 can also include one or more sensors 50. Useful sensors can be optical and chemical sensors. Such sensors can be used for measuring microenvironmental properties such as oxygen concentration, glucose concentration, cytokine concentrations or activity, metabolite concentrations and/or activity, and pH. In a refinement, sensor 50 can be a sensor coating that includes a luminophore or fluorophore and in particular, an oxygen-sensitive luminophore or fluorophore. An example of such an oxygen-sensitive luminophore is $Ru(Ph_2phen_3)Cl_2$. The sensor coating can also include an oxygen-insensitive fluorophore (e.g., Nile blue chloride) to be used as a control.

Figure 3:
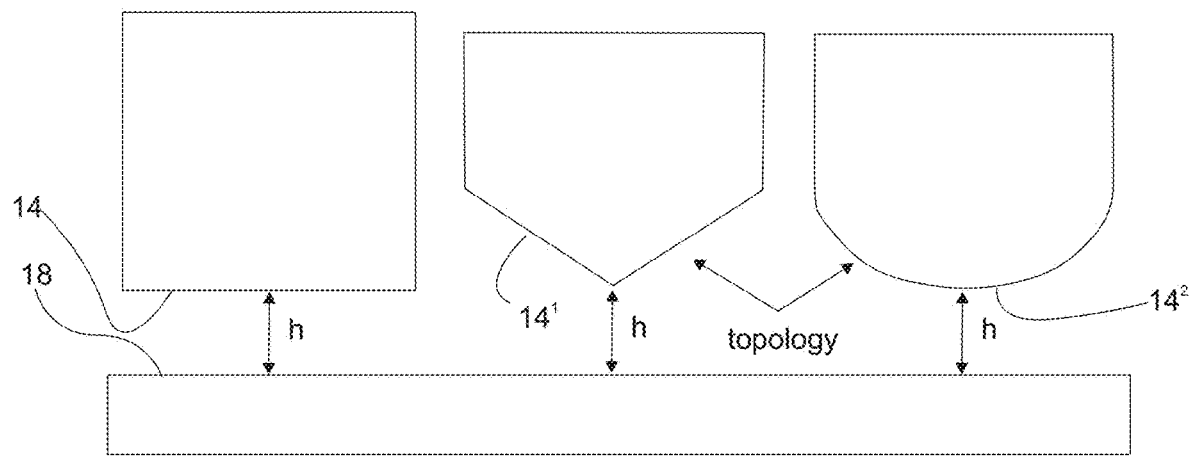
FIG. 3. Different topological shape of the diffusion barrier will alter the radial profile of oxygen concentration.

With reference to FIG. 3, a schematic illustration showing that the first space-defining surface 14 can have various topologies is provided. For example, the surface can be flat having a well-defined gap h between first space-defining surface 14 and second space-defining surface 18. In another variation, the gap is not constant with the first space-defining surface 14 having a cone ($14^1$) or curved ($14^2$) shape. These latter shapes can alter the radial profile of oxygen concentration.

Figure 4:
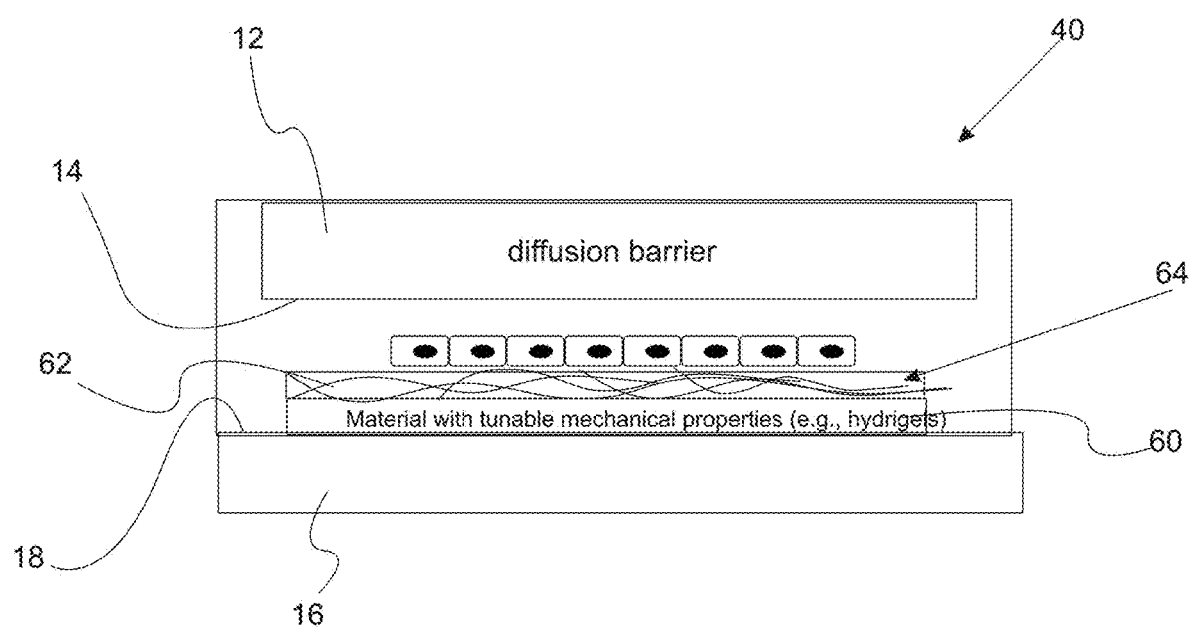
FIG. 4. Device can integrate extracellular component including the mechanical properties (using materials with tunable mechanical properties) or biochemical properties (using ECM coating).

FIG. 4 illustrates device 10 for inducing an oxygen concentration gradient which integrates extracellular components that can adjust mechanical properties (e.g., layer 60 with tunable mechanical properties) or biochemical properties (e.g., ECM coating 62) proximate to layer of living cells 22. Each of layers 60 and 62 can be interposed between layer of cells 22 and second space-defining surface 18. Examples of ECM materials that can be contained in coating 62 include, but are not limited to collagens (e.g., collagen I, collagen IV), fibronectin, hyaluronic acid, fibrin, fibrinogen, elastin, laminin, and combinations thereof. Moreover, the ECM materials can be embedded in extracellular matrix 64.

Figure 5A:
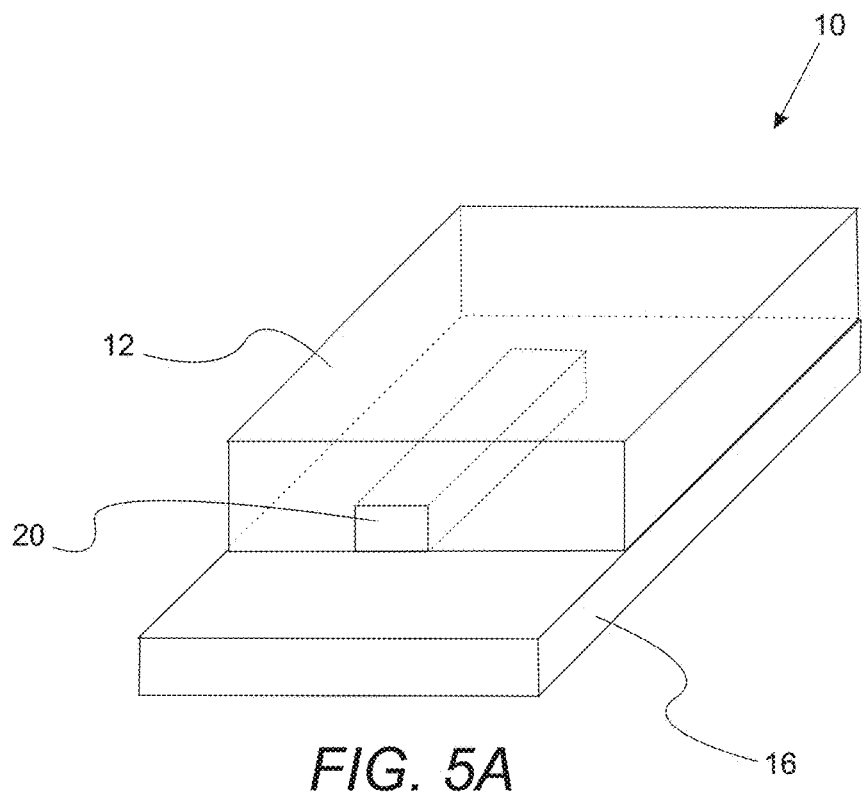
FIGS. 5A and 5B. Alternative shapes of microdevice with the same diffusion barrier concept. (A) Perspective view of a longitudinal channel; (B) Cross section of the longitudinal channel.
Figure 5B:
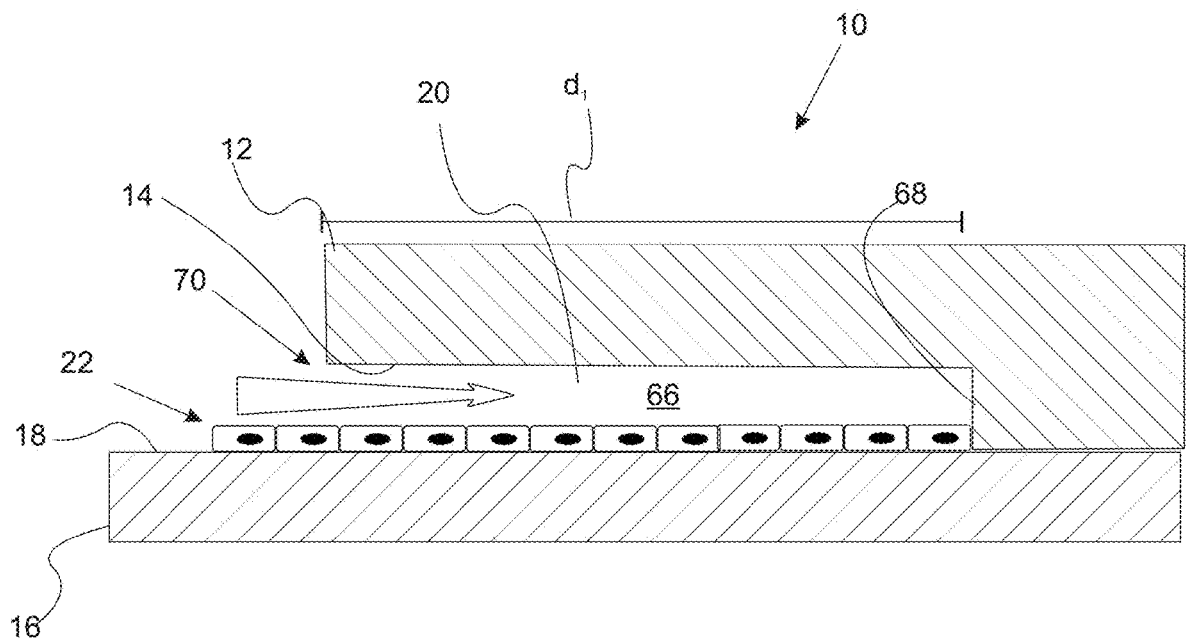

FIGS. 5A and 5B illustrate alternative shapes of a microdevice with the same diffusion barrier concept. In this variation, confined space 20 is a longitudinal channel 66 having a closed end 68 and an open end 70. In this variation, the length $d_2$ of channel 66 is from 1 to 25 mm. Moreover, the dimensions and area for layer of living cells 22 is the same as that set forth above.

Figure 6A:
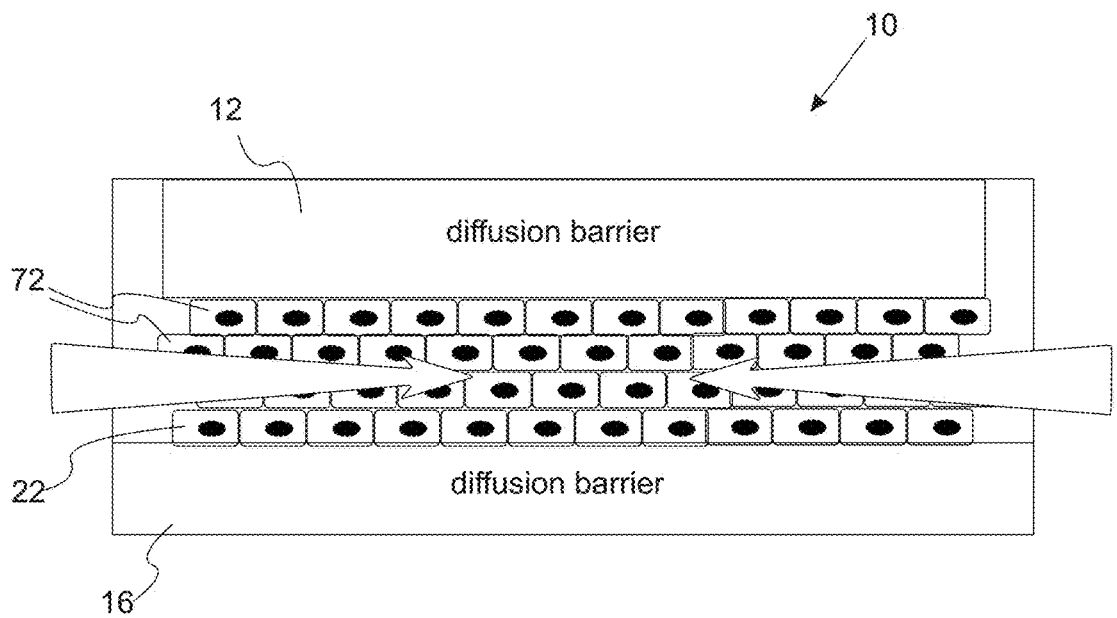
FIGS. 6A and 6B. Scaling cell culture from 2-D monolayer to 3-D bulk in the gap to allow tissue-like cell organization while maintaining control over diffusion profile. (A) Confined space with open ends or periphery; (B) Confined space that is a longitudinal channel with a closed end.
Figure 6B:
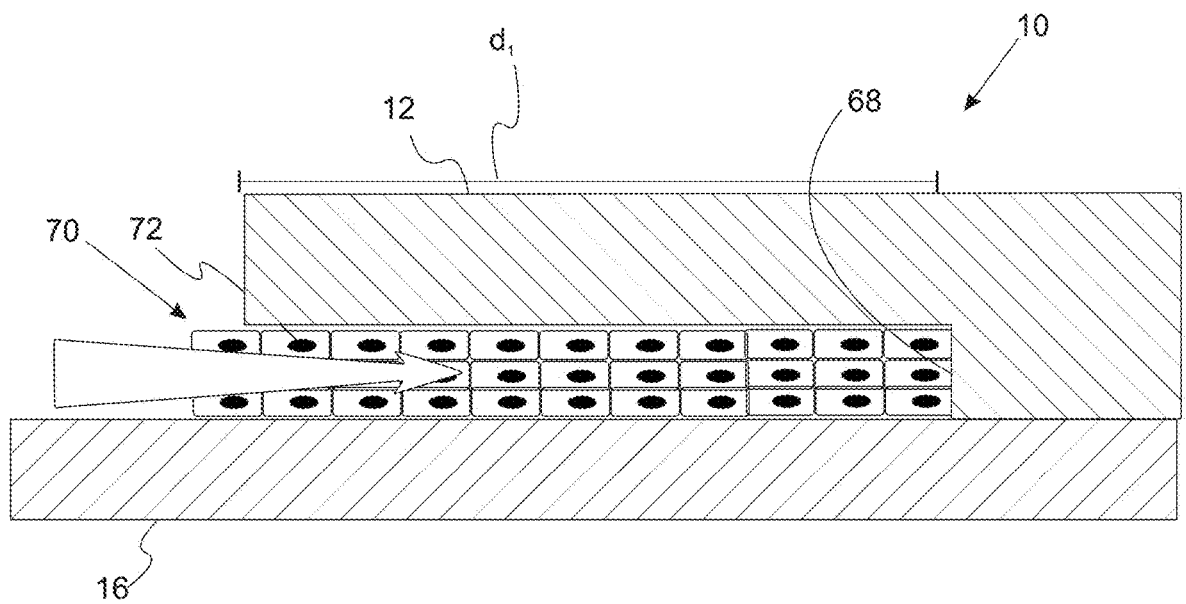

FIGS. 6A and 6B illustrate scaling to cell culture from 2-D monolayer to 3-D bulk in the gap to allow tissue-like cell organization while maintaining control over diffusion profile. In this variation, device 10 includes additional layers of living cells 72 disposed over layer of living cells 22 to build up a 3-D structure. In FIG. 6A, confined space 20 has open ends or periphery while FIG. 6B shows an example in which confined space 20 is a longitudinal channel 66 with a closed end 68. In this variation, the length $d_2$ of channel 66 is from 1 to 25 mm. Moreover, the dimensions and area for layer of living cells 22 is the same as that set forth above.

Figure 7A:
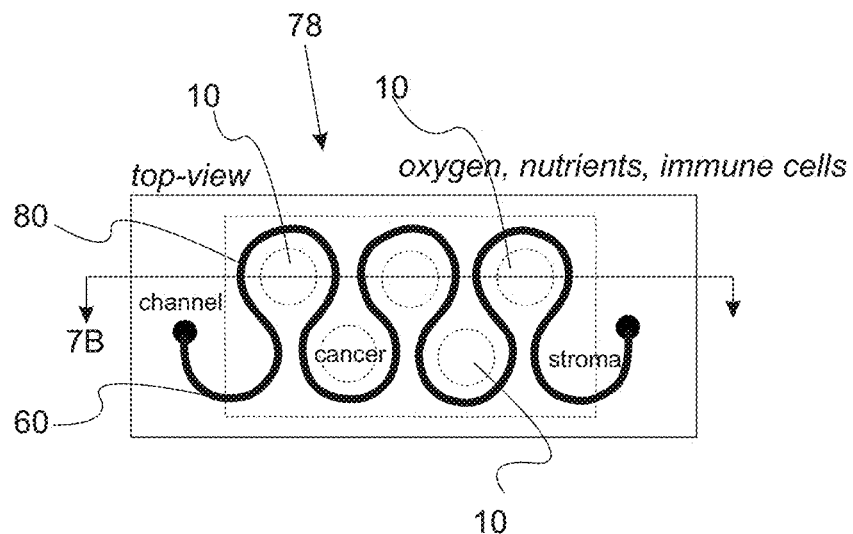
FIGS. 7A and 7B. Integration of the device with microfluidic channel and addition of endothelial cells mimic physiological delivery of soluble materials and cells (including drugs or therapeutic cells).
Figure 7B:
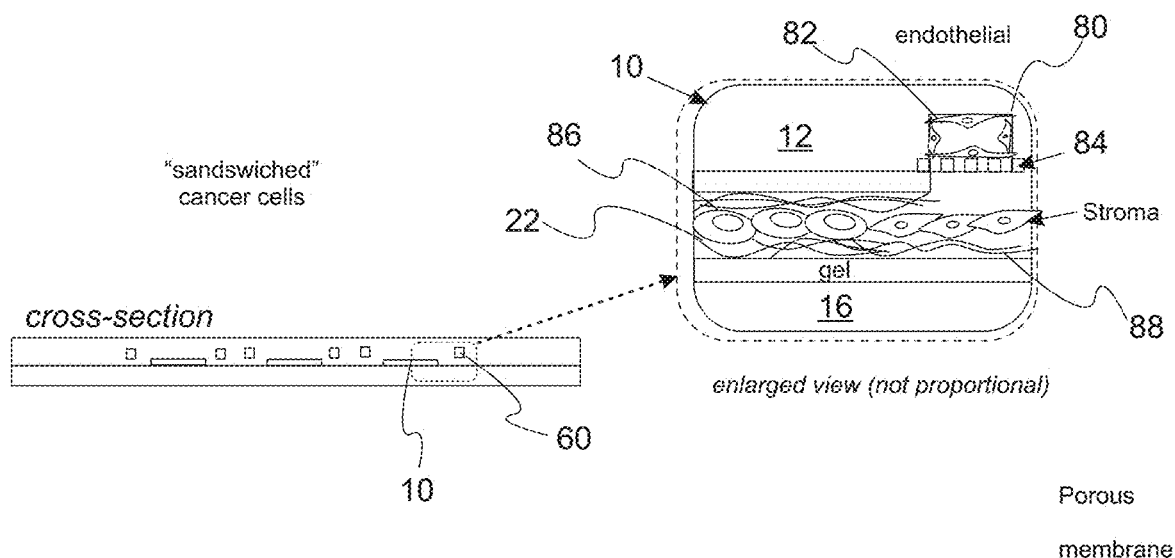

With reference to FIGS. 7A and 7B, schematics of an integrated system that incorporates the device for inducing an oxygen concentration gradient with microfluidic channels is provided. Integrated system 78 includes device(s) 10 and microfluidic channel(s) 80. In such variations, the microfluidic channel 80 is proximate to device 10 so that material can be delivered to layer of living cells 22. For this purpose, microfluidic channel 80 includes porous membrane regions 84 (e.g., PDMS) in fluid communication with confined space 20 and layer of living cells 22. In a variation, drugs and/or therapeutic cells are delivered to layer of living cells 22 via microfluidic channel 80. For example, endothelial cells 82 can be added to the microfluidic channel 80 to mimic physiological delivery of soluble materials and cells (including drugs or therapeutic cells). In a refinement, layer of living cells 22 can be interposed between layers 86 and 88 that include ECM materials as set forth above. In a refinement, microfluidic channel(s) 80 have a length from 1 to 50 mm. In another refinement, microfluidic channel(s) 80 have a length from 5 to 25 mm. In a further refinement, microfluidic channel(s) 80 have a cross sectional area from about 0.1 $mm^2$ to about 1 $mm^2$.

The following examples illustrate the various embodiments of the present invention. Those skilled in the art will recognize many variations that are within the spirit of the present invention and scope of the claims.

I. Results

Figure 1E:
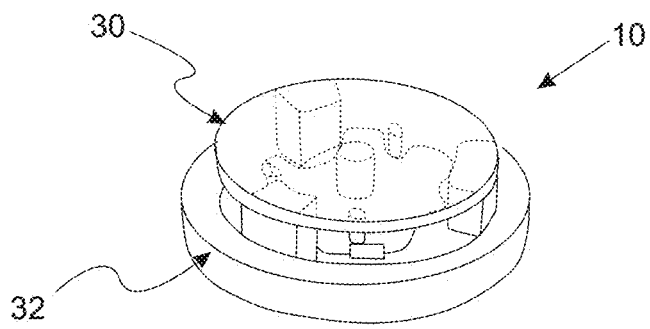

Diffusion barriers create an oxygen gradient in a cell layer. In a 3D tumor mass, a gradient of oxygen or hypoxia is established by the combined effects of cellular metabolism and oxygen diffusion. With the same concept, a "tumor-section"-like monolayer culture that incorporates "insulated" oxygen boundary conditions on both sides of the monolayer is introduced (FIG. 1A). Metabolic consumption and limited passive diffusion of oxygen in the gap between the two barriers will thus result in a gradient of oxygen and hypoxic levels in the monolayer (FIG. 1A). To achieve this theoretical induction of hypoxia, a microdevice using a computer numerical control (CNC) micro-milling platform is created with high precision at the microscale[34]. The microdevice consists of (1) a cap structure with a central pillar as an oxygen barrier and three reference pillars that determine the gap size for oxygen diffusion, and (2) a base structure that holds a culture substrate with a cell monolayer (FIG. 1B). In its assembled form, a DELRIN® base (white) holds a gas-impermeable glass coverslip with a cell monolayer to form the bottom diffusion barrier and the oxygen consumption layer; a polycarbonate pillar provides the other oxygen diffusion barrier as well as a transparent observation window for microscopy (FIG. 1E). Polycarbonate was chosen as the cap material due to its low oxygen permeability (polycarbonate: $9.1 \times 10^{-9}$ $cm^3/(cm^2\text{-sec-atm})$)[29,35-37] and excellent optical transparency[34].

Figure 8A:
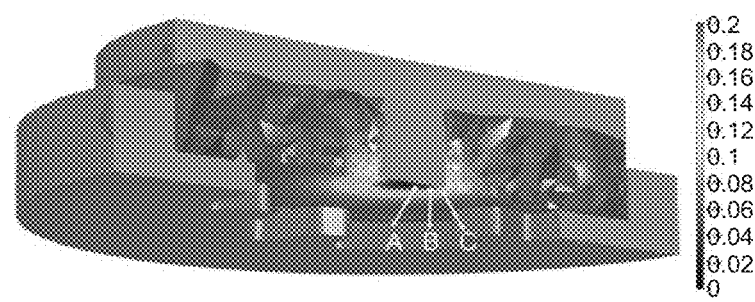
FIGS. 8A, 8B, 8C, and 8D. (A) Steady state oxygen in the hypoxia microdevice as a result of oxygen barriers and oxygen consumption by a micropatterned cell layer. (B) Evolvement of oxygen levels in the microdevice within 1,440 minutes of device assembly with the micropatterned cell monolayer. (C) Modulation of the steady state oxygen distribution by the gap size in a hypoxia microdevice. (D) Sensitivity of oxygen level at pillar center to gap sizes and radii of the oxygen barrier pillar.
Figure 8B:
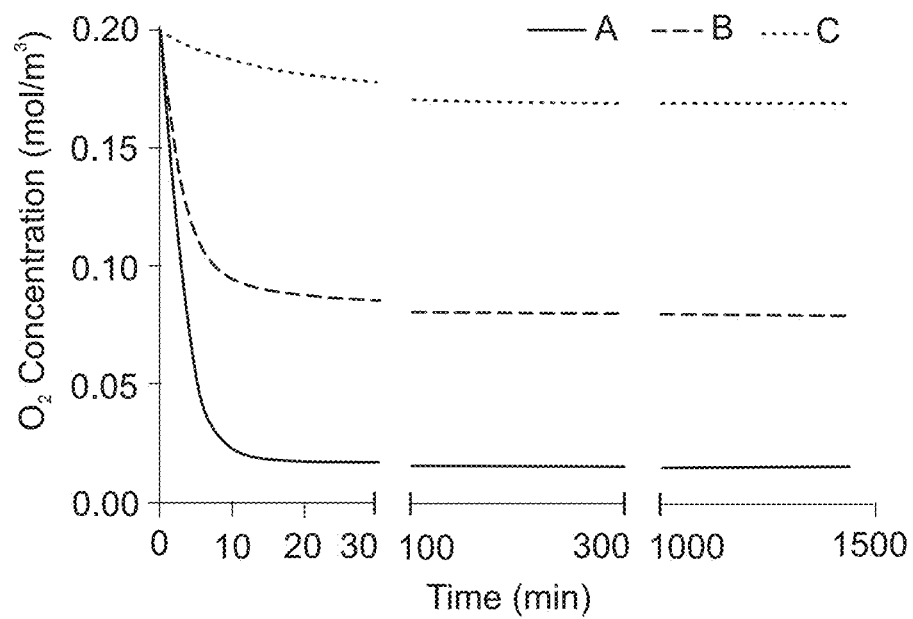
Figure 8C:
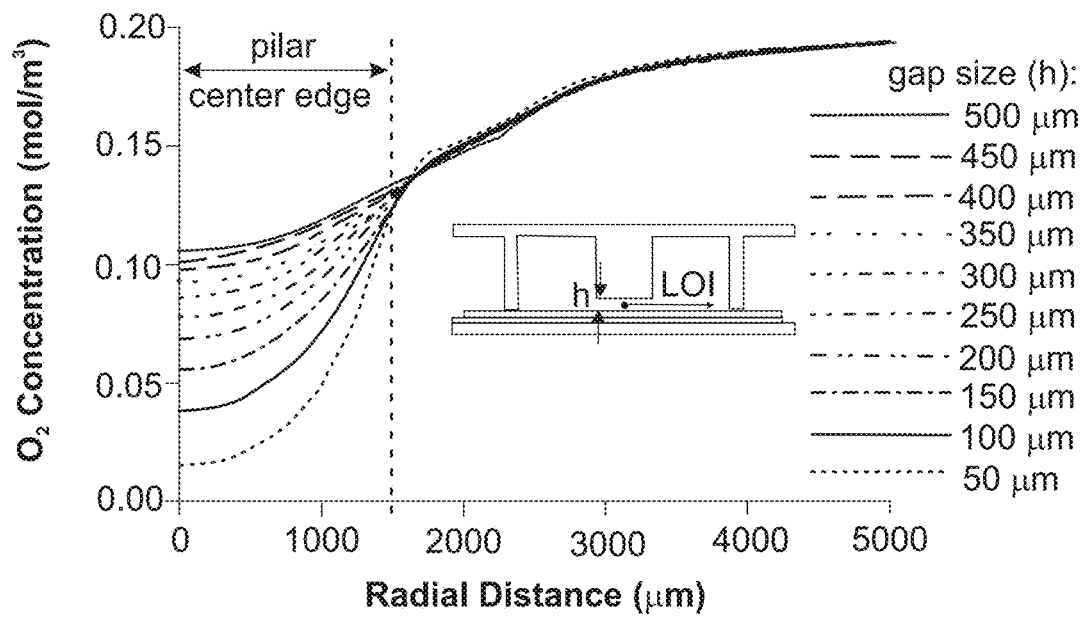
Figure 8D:
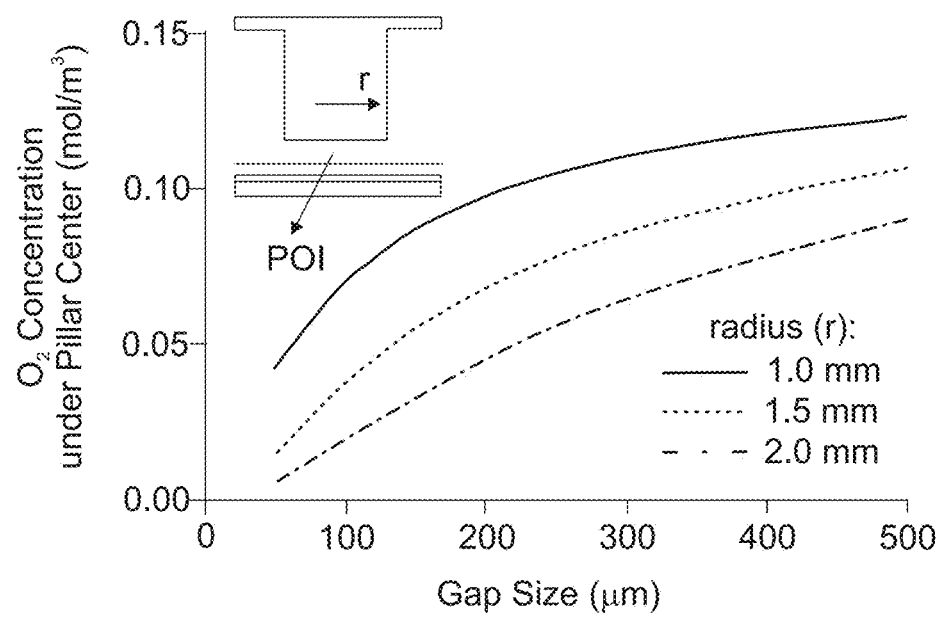

Computer simulations with COMSOL Multiphysics® was carried out to characterize the spatial and temporal profiles of oxygen expected in the hypoxia device. FIG. 8A demonstrates the steady-state distribution of oxygen in a microdevice with a 50 μm diffusion gap. The heat-map of oxygen concentration shows a radial transition of oxygen concentrations from near-zero under the center of the pillar to a normoxic level at the periphery. Three points of interest (POIs) were selected immediately above the cell monolayer: at the center (A), at the intermediate region (B) and at the edge (C) in relation to the pillar geometry (FIG. 8A). It was found that oxygen level within the device drops quickly within the first 10 minutes. Within 30 minutes, the oxygen levels are already within 92.8%, 93.3%, and 94.5% of the steady-state level at the locations A, B, and C, respectively. The influence of the diffusion gap size on the steady-state oxygen profile above the cell layer was then examined. This parameter is important for the design of the hypoxia microdevice, as actual oxygen level under the pillar can be influenced by the micro-milling accuracy of Δh. As shown in FIG. 8C, the radial oxygen distribution can be fine-tuned with Δh, where smaller gaps result in steeper oxygen gradients under the pillar. Oxygen gradient outside the pillar has little dependence on the gap size, suggesting that the device structure other than the pillar does not hinder oxygen supply from the bulk media and the media-air interface. The sensitivity of oxygen concentration to the pillar radii was further investigated. The oxygen level at the center in relation to Δh under pillars of different radii (FIG. 8D) was simulated. A larger radius increases the distance of oxygen diffusion, thus lowering the oxygen concentration in the center. COMSOL® simulation showed that in general, oxygen levels under smaller pillars are more sensitive to the changes in Δh (FIG. 8D). 1.5 mm was chosen as the pillar radius in the experiments to achieve biologically relevant hypoxic level[38,39], manageable imaging area for microscopy, and minimal sensitivity to the variation of Δh in micromilling[34].

Figure 9A:
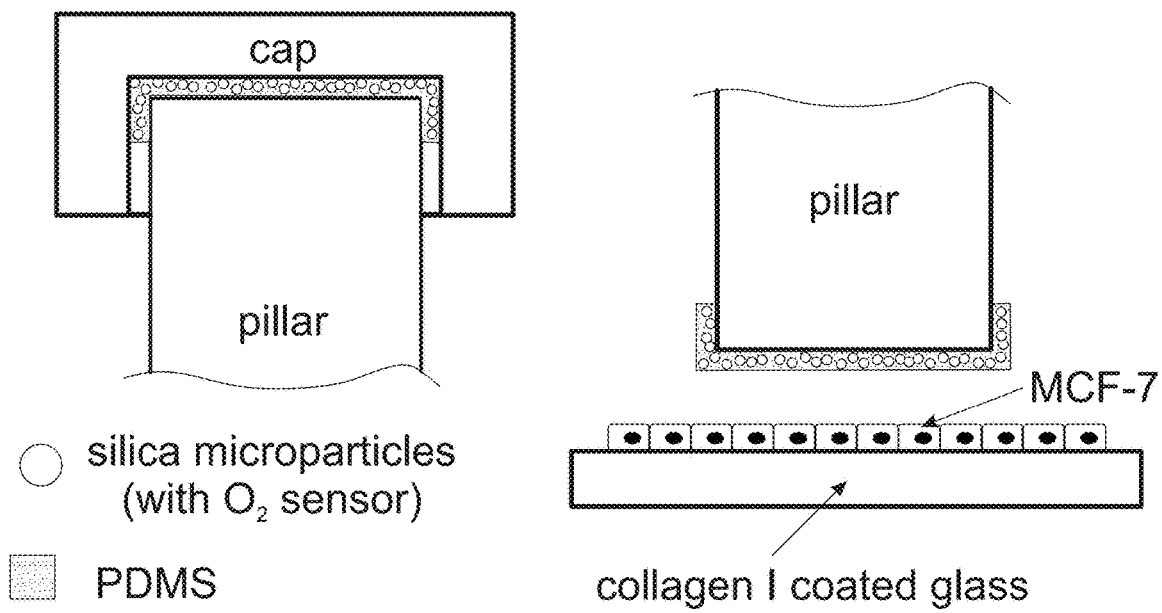
FIGS. 9A, 9B, 9C, and 9D. Oxygen levels in the microenvironment measured by an oxygen-sensitive fluorophore. (A) Schematics of oxygen sensor layer in the hypoxia device. (B) Fluorescent signal from sensor layer without or with the cell layer in the device. Scale bar: 500 µm. (C) Normalized fluorescent intensity of ruthenium compound by Nile blue in oxygen sensor particles over radial distance (center to edge) with and without cell layer from the same pillar. (D) Derived oxygen concentration under the pillar (orange, N=3) compared to simulated oxygen concentration (blue) show a good correlation (Pearson's correlation coefficient r=0.9458). Error bars: standard deviation (SD).
Figure 9B:
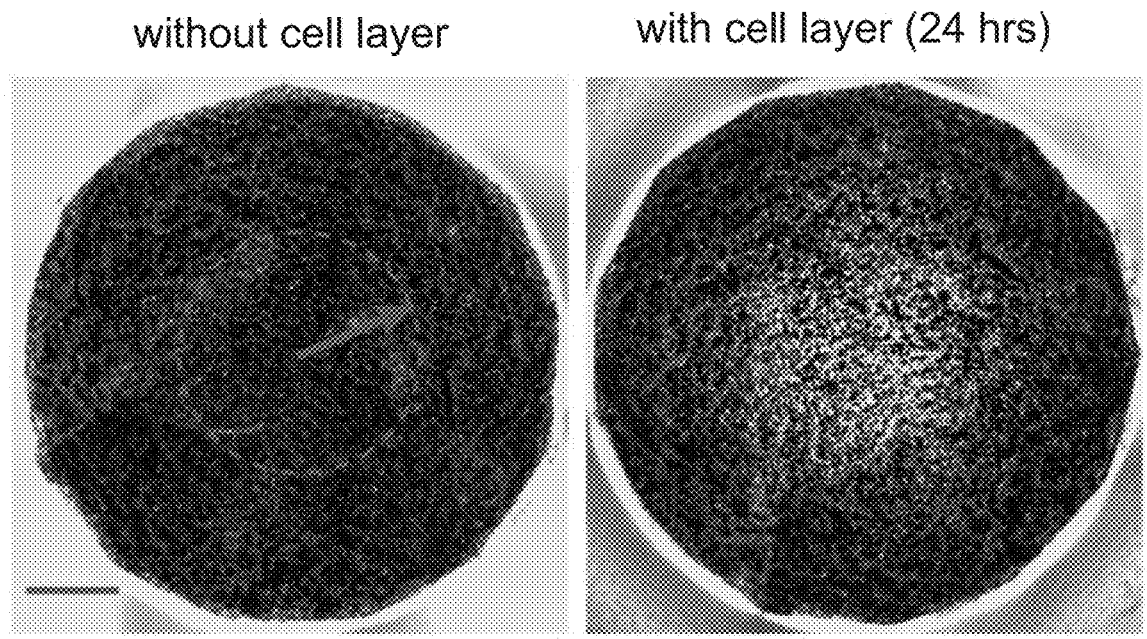
Figure 9C:
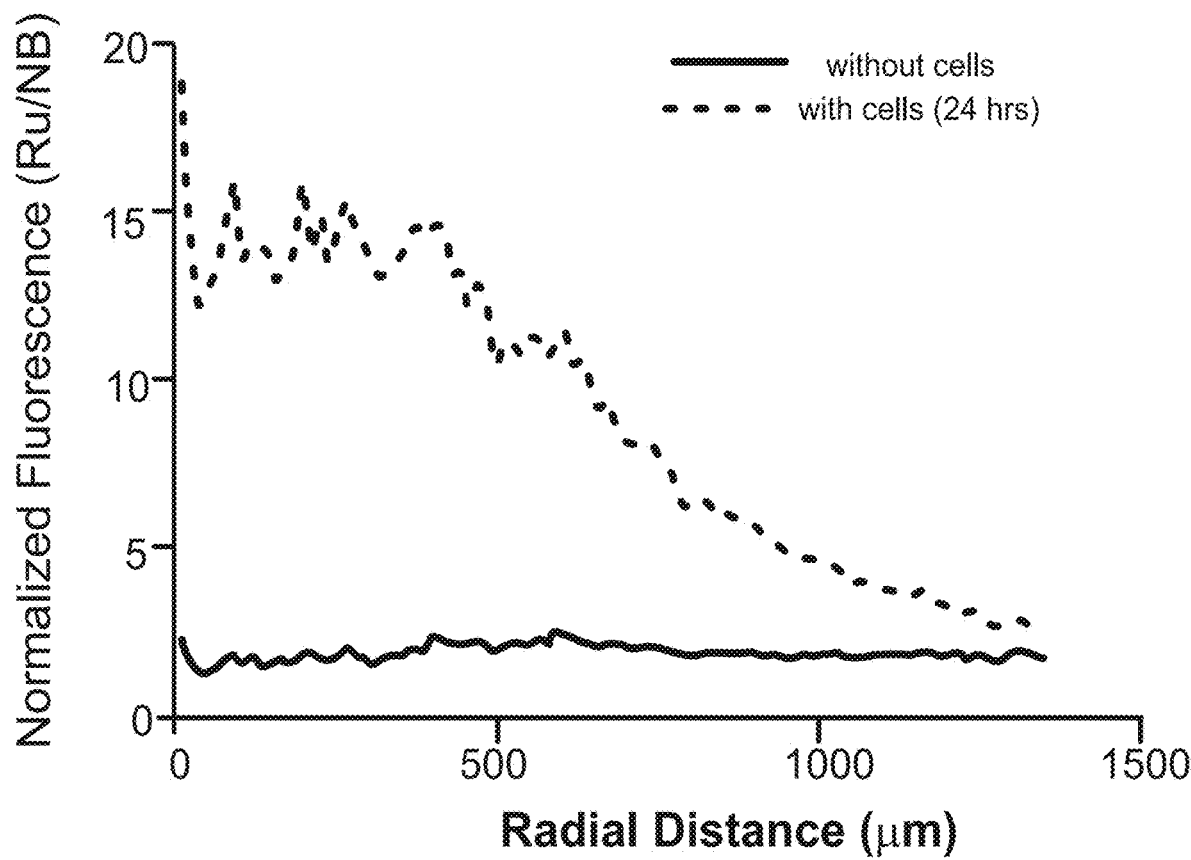
Figure 9D:
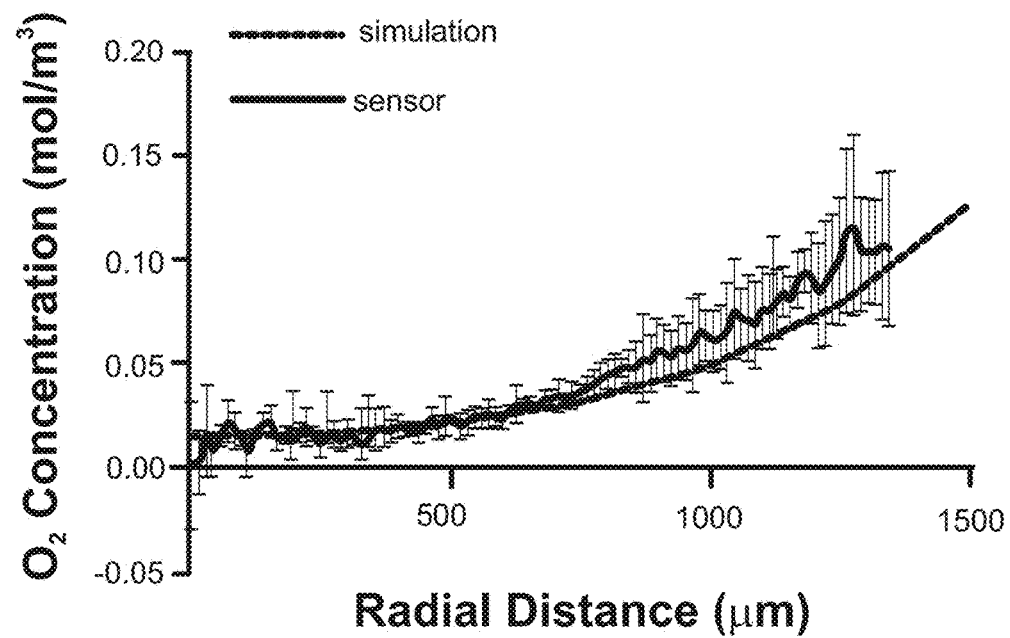

An integrated sensor layer can monitor the oxygen gradient. Next, cell culture experiments and characterization of the actual oxygen gradient by embedding a fluorescence-based oxygen sensor in the microdevice were performed. Silica microparticles were absorbed with an oxygen-sensitive luminophore $Ru(Ph_2phen_3)Cl_2$ (oxygen sensor) mixed with an oxygen-insensitive fluorophore, Nile blue chloride (control)[40]. They were then mixed in PDMS and spread in a thin layer onto the oxygen barrier pillar using a micro-milled cap (FIG. 9A, left panel). MCF-7 cells, a breast cancer cell line, were micropatterned on a collagen I coated coverslip in a circular island to mimic the morphology of cancer cell nests in a tumor tissue section[41], and assembled into the hypoxia microdevice (FIG. 9A, right panel). After 24 hours of cell culture, images of the silica microparticles in the respective fluorescent channels for the ruthenium compound and Nile blue chloride were obtained. Enhanced fluorescent signal from the ruthenium compound was observed near the center of the pillar in a radial distribution profile. In contrast, the same microdevice without the cell monolayer showed a relatively uniform, dim fluorescent signal (under the same imaging settings), which is consistent with the oxygen-quenching property of the ruthenium compound (FIG. 9B). Signal from Nile blue chloride, on the contrary, was insensitive to oxygen concentrations (data not shown). The normalized fluorescent signal (ruthenium by Nile blue, Ru/NB) was plotted against the radial distance without or with the cell layer from a single microdevice (FIG. 9C). Normalized fluorescence intensity was converted to oxygen concentration (N=3) and compared against the COMSOL® prediction, which shows a good match between the two (Pearson's correlation coefficient r=0.9458) (FIG. 9D).

Hypoxic Markers are Upregulated in the Microdevice.

Figure 10A:
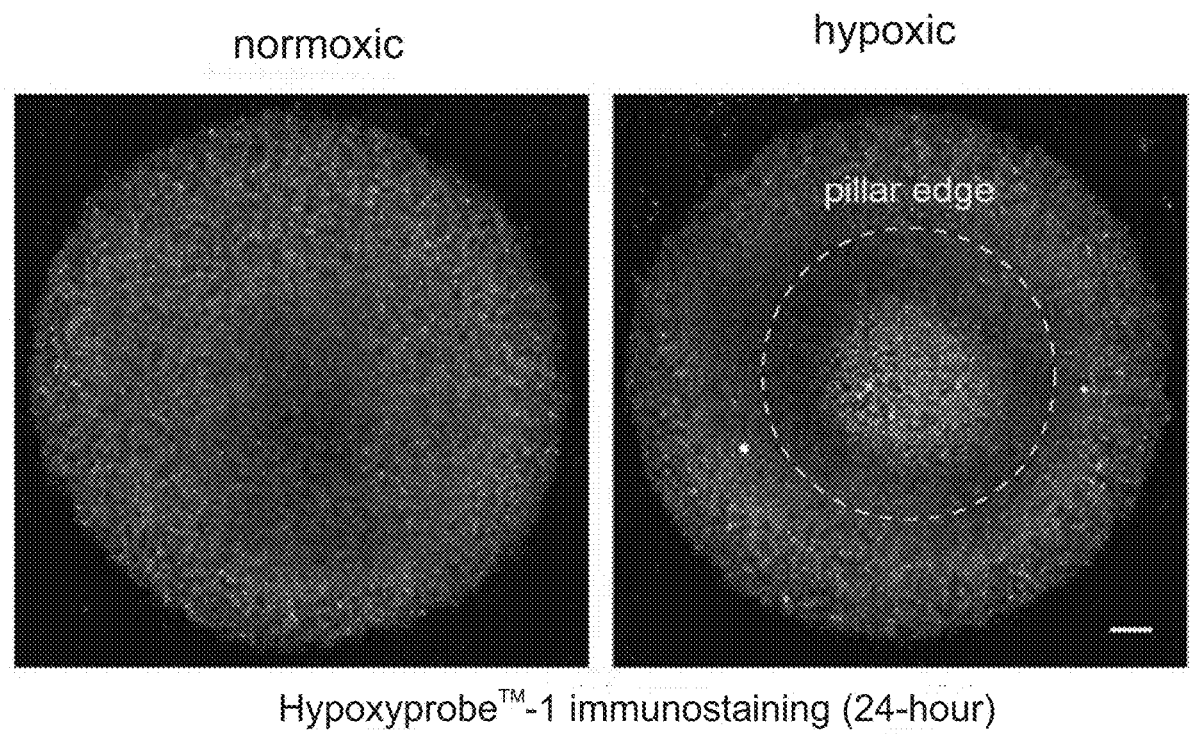
FIGS. 10A, 10B, 10C, and 10D. Upregulation of hypoxic markers in microdevice. (A) Hypoxyprobe™-1 immunostaining in micropatterned MCF-7 cells under normoxic condition and in hypoxia device after 24 hours of incubation. (B) Radial analysis of areal fractions with high Hypoxyprobe™-1 signal (normoxia: N=4; hypoxia: N=7). (C) Glut-1 immunostaining in micropatterned MCF-7 cells under normoxic condition and in hypoxia device after 24 hours (normoxia: N=5; hypoxia: N=8). (D) Radial profile of areal fractions with high Glut-1 expression. Scale bars: 500 µm. Error bars: SD.
Figure 10B:
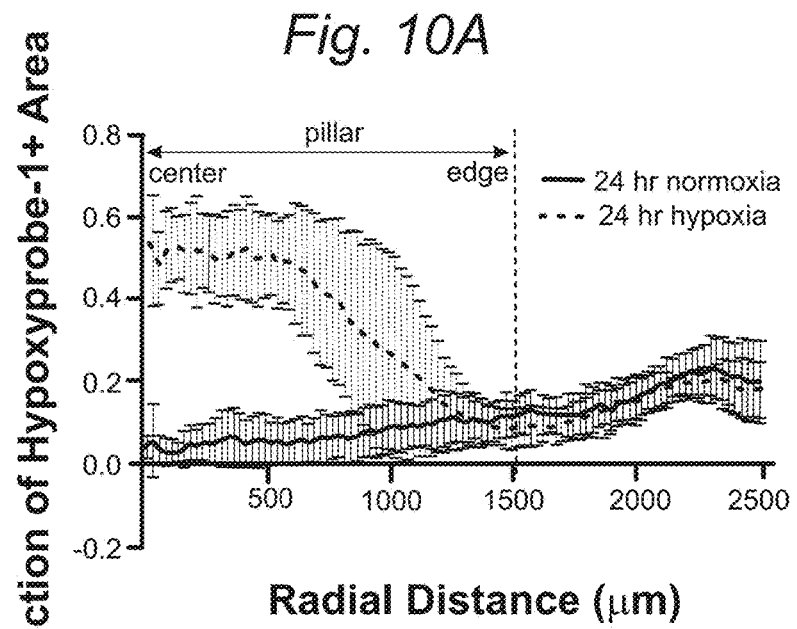

Immunofluorescent analysis on hypoxic markers was carried out to confirm that cells can create and respond to the oxygen gradient in the microdevice. Pimonidazole (also known as Hypoxyprobe™-1) is a chemical compound that can be reduced in hypoxic cells to form stable covalent adducts with thiol groups in proteins, peptides and amino acids, which can then be detected by immunofluorescent staining[42,43]. Elevated pimonidazole staining was detected under the pillar (FIG. 10A, B). Quantitative analysis (N=7) showed a signal plateau near the center of the pillar (in ~600 μm radius), with gradual decline to a background level near the edge of the pillar (from 600 to 1,300 μm). The oxygen concentrations corresponding to the two transition points are 0.028 and 0.08 mol/m³, respectively, based on the COMSOL Multiphysics® simulation.

Figure 10C:
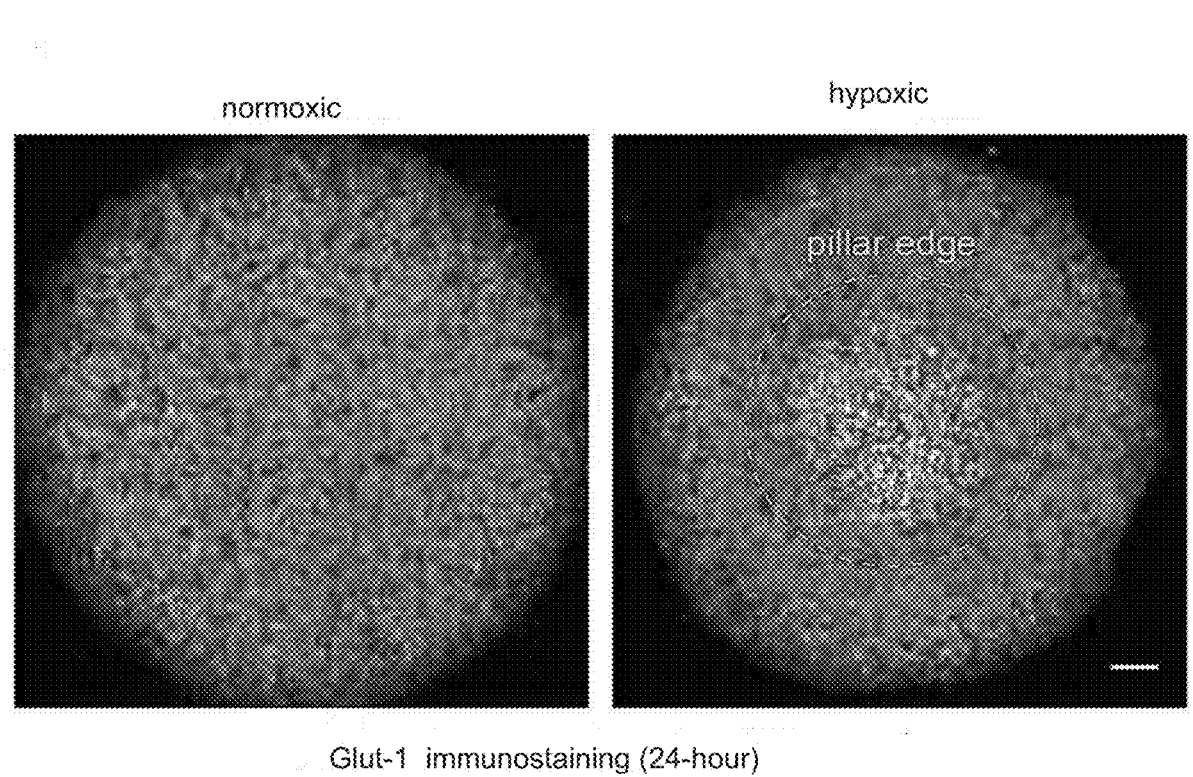
Figure 10D:
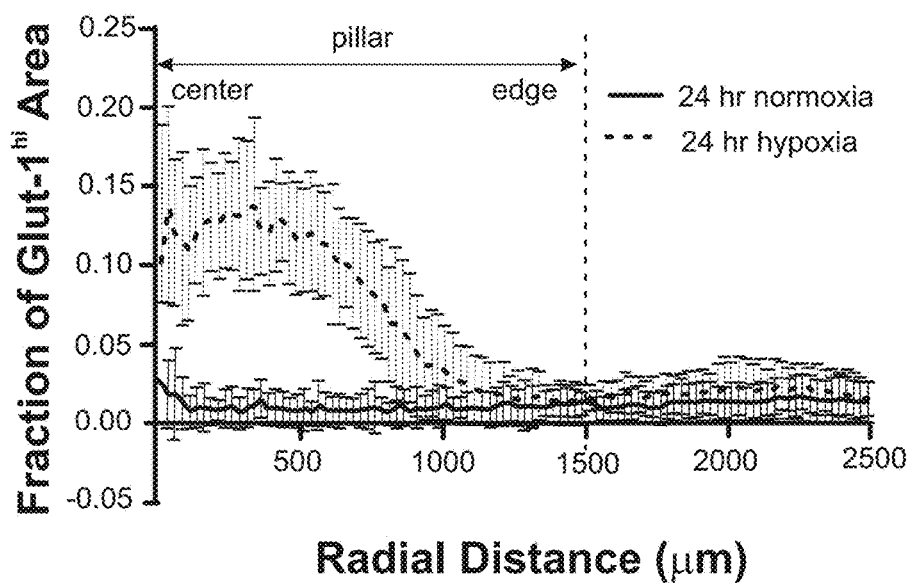

Glucose transporter-1 (Glut-1) is a glucose transporter protein that facilitates glucose supply into cells. It has been established as an intrinsic cellular marker for hypoxia and correlated with levels of reduced pimonidazole[44,45]. Glut-1 in the MCF-7 cells incubated for 24 hours in the microdevice were immunostained with distinct Glut-1 upregulation under the pillar being observed (FIG. 10C, D). A high degree of correlation was observed between the radial profiles of Glut-1 and reduced pimonidazole in the hypoxia device (Pearson's correlation coefficient r=0.9699), which agrees with previous findings[42].

Gene Expressions are Spatially Regulated in the Microdevice.

Figure 11A:
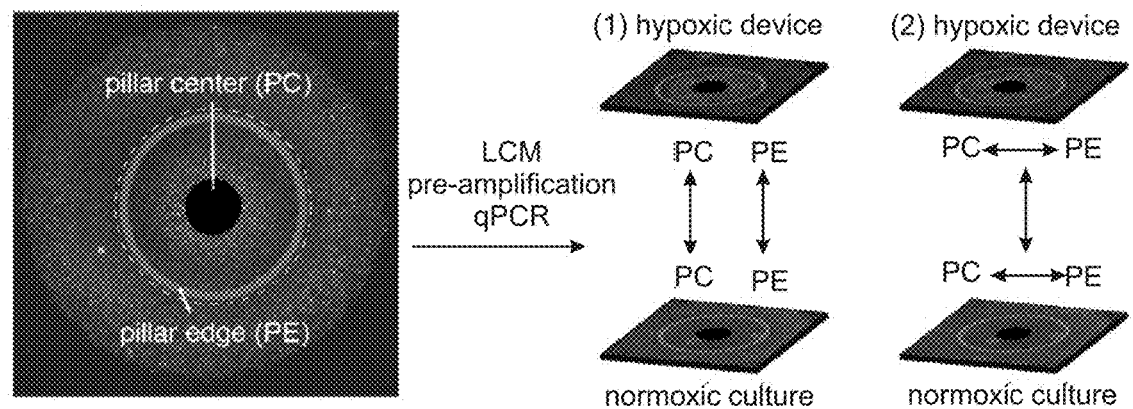
FIGS. 11A, 11B, and 11C. Gene expression analysis in hypoxia device. (A) Areal definition for laser capture microdissection in micropatterned MCF-7 cells under hypoxia device and two types comparisons of gene expression (1: hypoxia vs normoxia; 2: center vs edge). PC: pillar center; PE: pillar edge. (B) Region-by-region comparison between hypoxic and normoxic samples, and (C) In-sample comparison between center and edge areas under hypoxia device, with genes related to proliferation, apoptosis, glycolysis, and migration/metastasis. (B, C) N=3. Student's t-test: *$p<0.05$ for significant fold change in gene regulation; ‡$p<0.05$ for significant paired difference. All other conditions (non-labeled): not significant ($p>0.05$). Error bars: SD.

To investigate a wider range of pathways impacted by hypoxia in a spatially-resolved manner, the gene expression profiles of cells from micropattern regions under different oxygen levels in the device were analyzed. Cells were extracted with laser capture microdissection (LCM) from pillar center (PC) and pillar edge (PE), which represent hypoxic and near-normoxic (0.12~0.14 mol/m³ by simulation) regions, respectively (FIG. 11A). Gene expression was compared in two ways: (1) both PC and PE regions in the hypoxia device were compared to their corresponding regions in the normoxic samples, and (2) PC was compared to PE in the same samples under the respective normoxic or hypoxic conditions. Gene targets were selected to include a diverse range of cellular functions, including cell proliferation (MK/67)[46], apoptosis (BNIP3, DDIT4)[47,48], glycolytic metabolism (SLC2A1, CAIX, PGK1)[45,47,48], and migration/metastasis (SNAI1, VIM, CXCR4)[49,50].

Figure 11B:
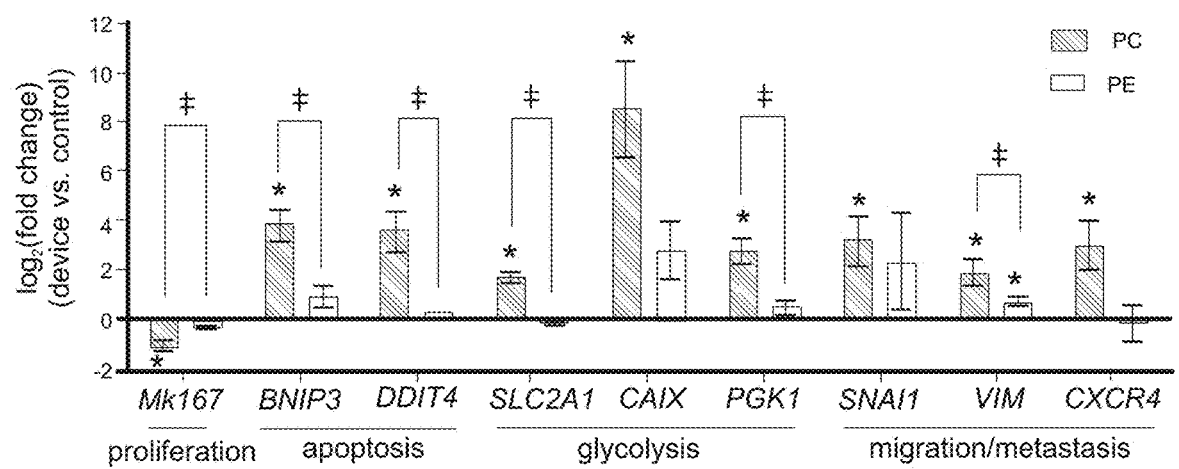
Figure 11C:
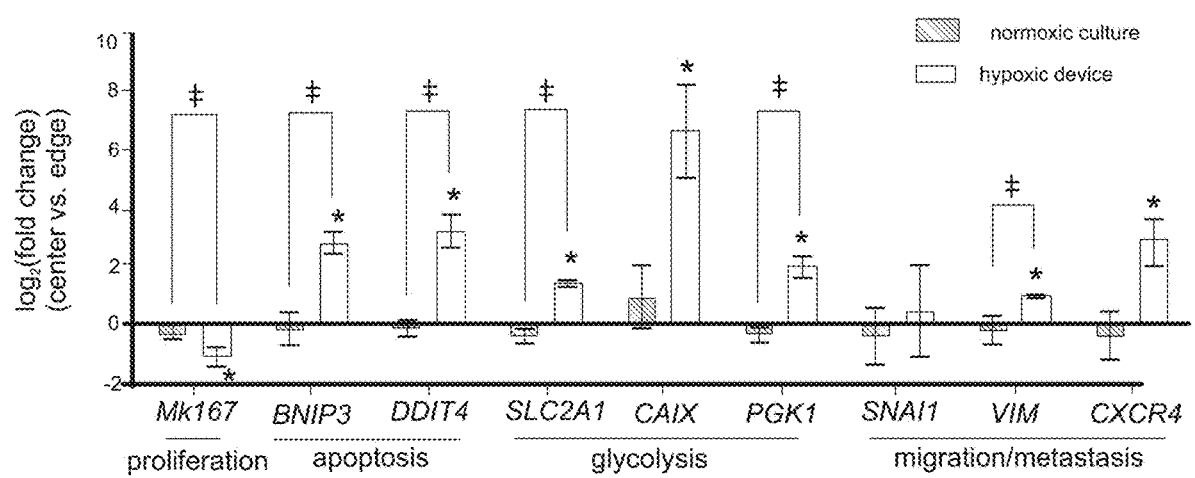

When normalized to their normoxic counterparts, cells in hypoxic PC regions have down-regulated proliferation and up-regulated expression of genes related to apoptosis, glycolysis, and migration/metastasis (blue bars, p<0.05, Student's t-test, FIG. 11B). In contrast, the same analysis shows no significant up- or down-regulation of the same set of genes in the PE regions (orange bars, p>0.05, Student's t-test, FIG. 11B). When the differential gene expression between PC and PE in the same samples was analyzed, it was discovered that the gene expression in the cells from the hypoxia device are spatially regulated by the oxygen gradient, with down-regulated proliferation and up-regulated markers in PC for apoptosis, glycolysis and migration/metastasis (except SNAP) (orange bars, p<0.05, Student's t-test, FIG. 11C). Similarly, the same analysis shows that there is no spatially resolved differences in gene expression in normoxic samples (blue bars, p>0.05, Student's t-test, FIG. 11C).

Spatially Resolved Drug Response is Observed in the Device.

Figure 12A:
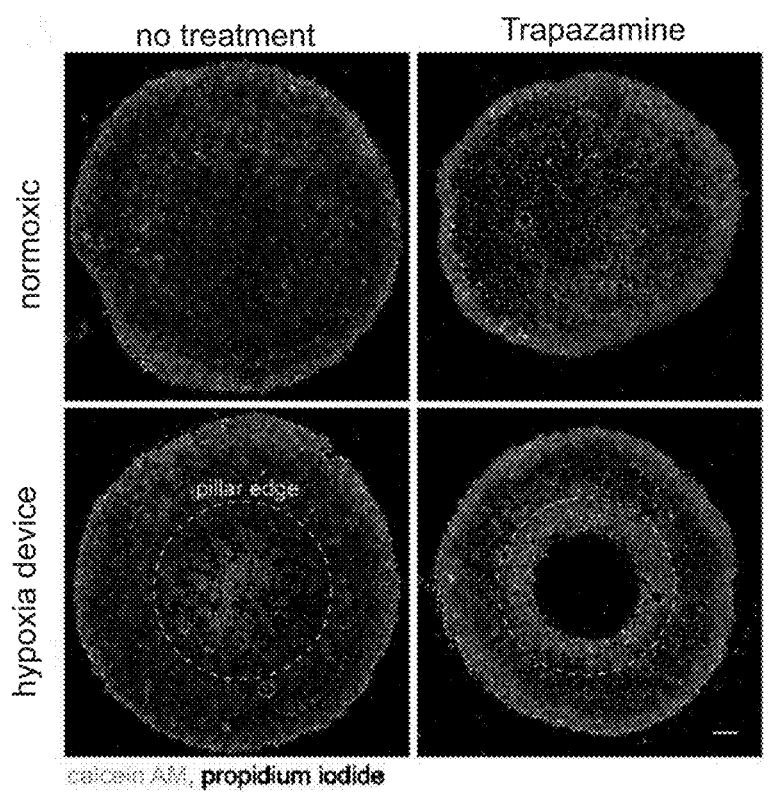
FIGS. 12A, 12B, and 12C. Cellular response to hypoxia-targeting drugs in hypoxia device. (A) Live-dead staining of micropatterned MCF-7 cells under normoxic condition or in hypoxia device, without treatment or under the treatment of tirapazamine (TPZ), a drug targeting hypoxic cells. Green: live (calcein); red: dead (propidium iodide). (B) Areal density of live (green) and dead (red) cells in the micropattern along the radial direction. (C) Proportion of live cells in the inner/pillar region versus outer region (N=3). One-way ANOVA; n.s.: not significant ($p>0.05$). Error bars: SD.
Figure 12B:
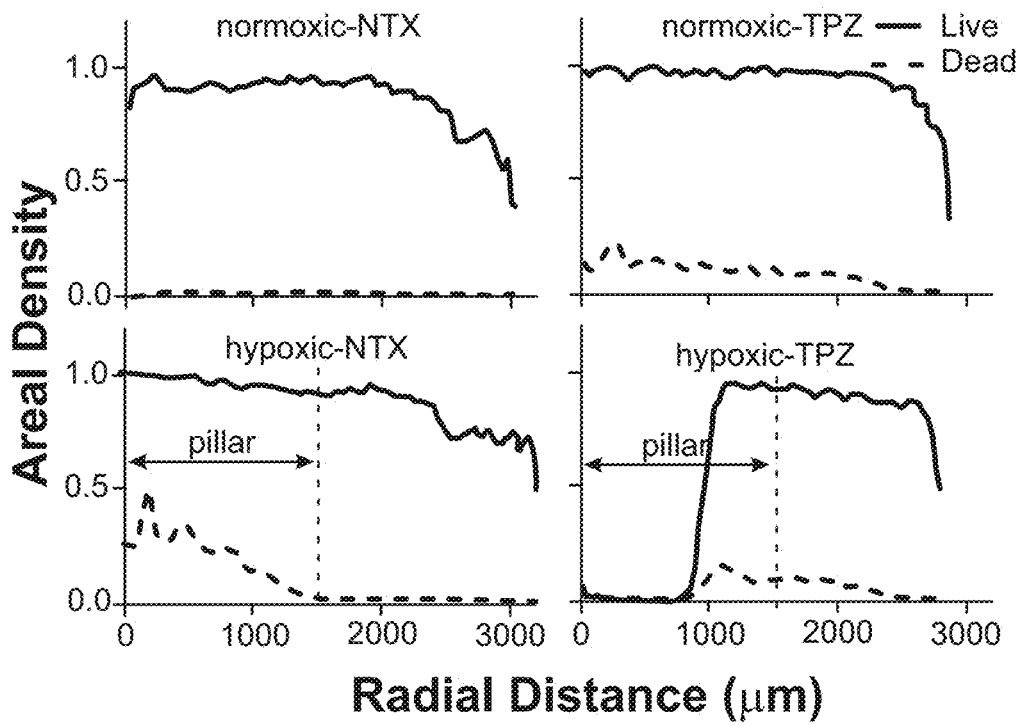
Figure 12C:
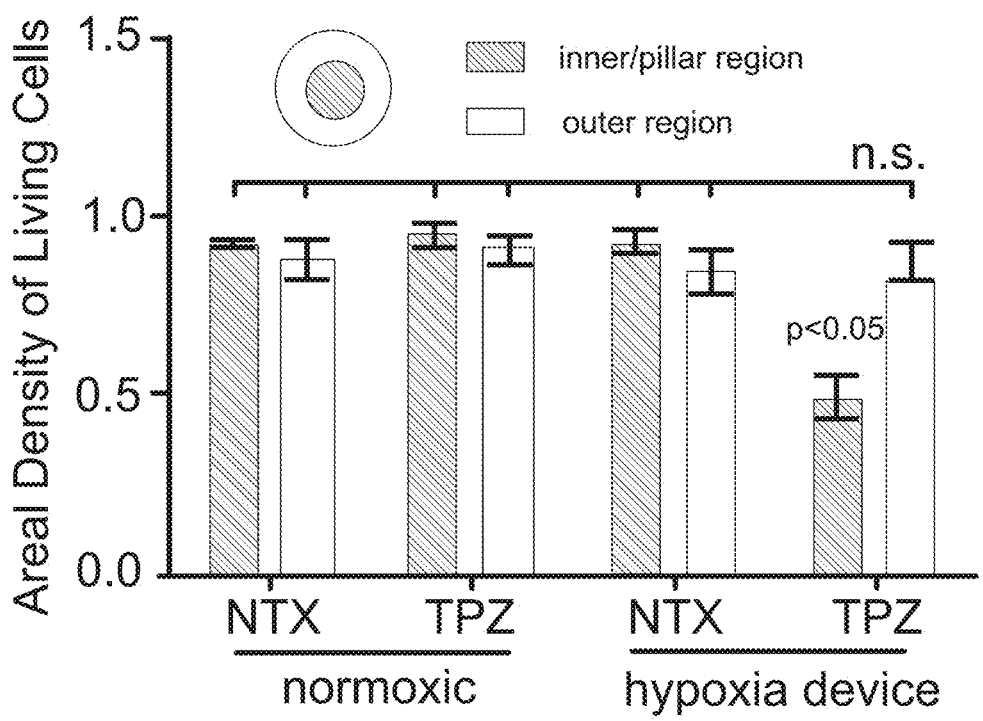

To assess the response of cancer cells to drug treatment under a hypoxic gradient, as well as the feasibility of the microdevice for drug screening assays, cell viability assays with TPZ treatment in the microdevice were performed. TPZ is an experimental anticancer prodrug that is 15- to 50-fold more selective at targeting hypoxic human cancer cells than their normoxic counterparts[51,52]. Cells were pre-conditioned with hypoxia in the microdevice for 12 hours, which was considered sufficient to induce cellular adaptations to hypoxia[47], before being treated with TPZ for 24 hours. The TPZ concentration that inhibit 50% of the cancer cell growth (IC50)[53] and differentially kill hypoxic cells over normoxic cells in the dosage test was used. Live-dead staining revealed cytotoxicity caused by TPZ in both normoxic and hypoxic samples indicated by positive nuclear propidium iodide (PI) staining (FIG. 12A, tirapazamine column, and corresponding radial distributions in FIG. 12B). Non-treated cells under deep hypoxia also showed pronounced cell death (FIG. 12A, B, lower left panel). Most strikingly, cells under severe hypoxia (corresponding to ≤0.03 mol/m$^3$ oxygen level by COMSOL® simulation) in the microdevice were eliminated by TPZ treatment (FIG. 12A, B, lower right panel). As dead cells can be washed off in the staining process, the areal fraction of living cells with positive calcein staining was chosen as the readout for TPZ cytotoxicity. The live-cell fractions in the micropatterns inside and outside the 1.5 mm radius were quantified, which corresponds to the pillar radius. TPZ treatment caused significant reduction in the live-cell fraction only in the hypoxia microdevice, while all other conditions were not statistically different from each other (FIG. 12C, one-way Analysis of Variance, ANOVA).

DISCUSSION

Embodiments of the present invention introduce a novel microdevice platform to study tumor microenvironment under a hypoxic gradient. It can accurately generate and control oxygen gradients, eliminates complex microfluidic fabrication and handling, allows for incorporation of additional tumor components, and is compatible with high-content imaging-based analysis and high-throughput applications. These features have only been partially achieved by other individual platforms[24,27-33]. By combining cell-driven oxygen consumption and controlled passive oxygen diffusion, the microfluidic components commonly used by others[21,54] is eliminated, thus greatly simplifying the design of the microdevice and cell culture operations. The lateral oxygen gradient created on a monolayer cell culture also allows for real-time, high-content investigation of cellular phenotypes and behaviors with wide-field microscopy-based techniques, as demonstrated by the LCM-based gene expression analysis. This simplicity and compatibility will likely facilitate the adoption of the methods of the invention in biological research laboratories that usually lack engineering equipment or expertise to handle microfluidic devices, as well as in pharmaceutical industry that requires simplicity, scalability, and reproducibility[55,56]. The experiments demonstrated the use of the platform for cell micropatterns larger than the pillar so that cells outside the pillar can be referred to as an internal normoxic control, and for up to 36 hours of cell culture (12 hours of conditioning and 24 hours of TPZ treatment), which is sufficient to induce gene and protein expressions as well as drug response. Notably, the platform for a growing "tumor nest" culture was adapted by culturing cell micropatterns smaller than the pillar, which has a co-evolving hypoxic gradient with the growing cell island. Cell cultures were extended to 96 hours to capture additional hypoxic responses. Moreover, the platform can also be used beyond cancer to study other biological processes and cell types affected by hypoxia, such as the differentiation of embryonic stem cells[57] and induced pluripotent stem cells (iPSCs)[58], wound healing[59], and immunoediting[60,61].

Micro-milling was used to fabricate the hypoxia microdevice as set forth above. The technique allows for materials with desired (low) oxygen permeability, which is not attainable with PDMS in conventional soft lithography[62]. Importantly, a unique strength of the device and fabrication is that the diffusion barrier pillar can be milled with flexible sizes (e.g. lateral or gap dimensions), arbitrary geometries (e.g. squares, ovals, or those mimicking real tumor shapes) and topologies (e.g. conical or spherical shapes) to alter the overall oxygen distribution in the gap. With the assistance of computer simulation, oxygen distribution profiles in the microdevices can be designed to reflect the heterogeneous oxygen landscape in tumors with various sizes and cancer types, and at different stages[39,63]. As a rapid prototyping technique, micro-milling also allows for quick iteration of design parameters. On the other hand, once the parameters are set for a given study or application, alternative fabrication approaches such as inject molding can be utilized to fabricate the microdevice in large scales[64].

Another important feature of the tumor microdevice platform is in its ability to incorporate additional components and features of tumor microenvironment. For example, the collagen I coating can be replaced with other ECM types (e.g. collagen IV, fibronectin, hyaluronic acid, etc.) that play unique roles in cancer progression and therapeutic resistance[65,66]. The glass substrate can be supplemented with a layer of elastic material (e.g. acrylamide gel[67] or PDMS micropillar array[68]) to understand the interplay of cellular mechanics with hypoxia. Additional cell types, such as immune cells and fibroblasts can be incorporated to reveal their crosstalk with cancer cells in an oxygen gradient[41]. While the experiments focused on 2D monolayer cultures, integrating scaffold biomaterials and bioprinting techniques to create thin-layer 3D cultures in the platform to further recapitulate cellular behaviors unique to 3D cultures can also be implemented[69].

Finite element analysis through COMSOL Multiphysics® was extensively used to simulate oxygen levels and distributions in the microdevice, to confirm the concept and adjust the design in the experiments set forth above. It is noteworthy that the fidelity of the simulation to reality is dependent on the physical parameters used in the model[70]. One of the key parameters is the oxygen consumption behavior of the cells. An oxygen consumption rate of MCF-7 cells reported by others[63] was used. For hypoxic conditions, previous reports[70,71] were followed to assume that the cells have a Michaelis-Menten-type consumption rate depending on the actual oxygen levels (above a critical value), which drops to zero when oxygen level falls below the critical value[70]. To mimic a more realistic spatiotemporal oxygen profile, commercial assays (such as the Seahorse assay[72]) can be used to further validate or replace the concentration-dependent oxygen consumption equation for given cells of interest.

To complement the numerical simulation, the oxygen distribution in the microdevice was measured with microparticle-based oxygen sensors embedded under the pillar. It should be noted that the oxygen sensor particles showed highly variable fluorescent signals near the center of the pillar where deep hypoxia is induced by the cell micropattern (FIG. 9C, orange curve). There was also high variability of fluorescence intensity, calibration curves, and oxygen measurement from different devices (seen as high standard deviation, SD in FIG. 9D). Therefore, in its current form, the oxygen sensor layer method is still only a semi-quantitative analysis. The model also did not consider the photobleaching of the luminophore and the distribution of the ruthenium material in the silica and silicone phases of the sensor layer, which have been suggested to influence the linearity and sensitivity of the measurement[73]. In the future, the measurement may be improved by adopting a two-site oxygen binding model for the multi-phase sensor layer[40,73]. On the other hand, the fluorescence lifetime of the ruthenium-based oxygen sensors is also dependent on oxygen levels dictated by a similar Stern-Volmer model[40,73]. Since the lifetime of fluorescence is an intrinsic property of a fluorophore and independent of fluorescent intensity[74], fluorescence lifetime imaging microscopy (FLIM) can be used to more accurately measure the oxygen levels[75]. It is important to note that a gradient of nutrients and soluble factors can be similarly induced by cellular metabolism and biological activities. Moreover, chemical and optical sensors to measure other microenvironmental factors such as glucose[76], cytokines[77], metabolites[78], and pH[79] can be integrated into the microdevice.

The microdevice set forth herein can capture the spatial heterogeneity of cellular phenotypes induced by a hypoxic gradient. Molecules and proteins regulated by hypoxia can be immunostained and correlated with the oxygen gradient, as seen in the Hypoxyprobe-1™ and Glut-1 staining (FIG. 10). As a proof-of-concept, the platform was interfaced with LCM, another microscopy-based technique, to analyze the spatial profile of gene expressions related to a wide range of biological behaviors (FIG. 11). With next-generation sequencing and proteomic technologies[80,81], it will allow for transcriptome- and proteome-level analysis of the hypoxic tumor microenvironment on a single-cell level, and reveal signaling network and crosstalk linked to cancer progression and therapeutic response. These include, but are not limited to, cellular metabolism[82], CSCs[83], EMT[84], radioresistance[82], as well as biomarkers related to disease prognosis[45,82].

The cytotoxic effects of TPZ were confirmed in an experimental drug that is preferentially activated in hypoxic environments[85], on cancer cells experiencing a hypoxic gradient (FIG. 12). A striking "death zone" near the center of the pillar under TPZ treatment was observed, with a sharp boundary between the dead and live cell area. The result suggests the highly selective nature of TPZ treatment on cells below a hypoxic threshold. Notably, increased cell deaths in untreated hypoxic samples was observed (FIG. 12A, B, lower left panel) in agreement with the gene expression data that indicate enhanced apoptosis in the PC region against the PE region and the normoxic control (FIG. 11B, C). TPZ-induced cytotoxicity in the normoxic samples under the 50 μM TPZ treatment condition (FIG. 12A, B, upper right panel) was also observed, which is consistent with the TPZ-mediated cell killing in normoxic cultures in the dose-response measurement. Interestingly, calcein signal in the live-dead staining was preferentially enhanced in the central hypoxic areas, at the edges of the "death zone", and at the periphery of micropatterns. It may be attributed to reduced self-quenching of calcein dye in more extended cells[86] as a result of increased growth areas due to micropattern edge effect or dead neighboring cells, or reduced expression of multidrug transporter[87]. To minimize the influence of calcein fluorescence intensity in the quantification, areal fraction of positive calcein staining, instead of the total intensity, was thus calculated for FIG. 12C. Future experiments on TPZ dosage and its relation to the radii of the "death zone" can further reveal the adaptability of the drug to different hypoxic levels. The microdevice can also be used as a drug testing/screening platform to assess the efficacy of combinatorial treatments with chemo-, targeted- and immuno-therapeutic drugs to eradicate heterogeneous cancer populations in the hypoxic tumor[88], to accelerate the discovery of more effective cancer drug regimens.

In summary, a tumor microdevice platform that recapitulates the hypoxic gradient in tumor microenvironment for high-content and high-throughput applications is provided. The establishment of the oxygen profile through multiphysics simulation was demonstrated by optical sensor measurement, immunostaining, spatially-resolved gene expression analysis, and hypoxia-targeted drug treatment. It is compatible with high content imaging, live-cell tracking, and single-cell analyses. It is also adaptable with additional microenvironmental components and biosensors. The invention's flexible and scalable platform will allow for extensive investigation of tumor biology and other hypoxia-related biosystems, and also serve as a powerful tool for therapeutic discoveries.

II. Materials and Methods

Cell Culture and Micropatterning.

MCF-7 human breast cancer cells were purchased from ATCC and maintained in Dulbecco's Minimum Essential Medium (DMEM; Thermo Fisher) supplemented with 10% fetal bovine serum (FBS; Omega Scientific), 100 U mL$^{-1}$ penicillin, and 100 μg mL$^{-1}$ streptomycin (Thermo Fisher), in a humidified incubator maintained at 37° C. and 5% $CO_2$. Round glass coverslips (12 mm in diameter; Fisher Scientific) were immersed in hot commercial detergent, rinsed with deionized water, and dried with air. The coverslips were then treated with plasma (Harrick Plasma, Model PDC-001-HP) and silanized with 1% aminopropyltriathoxysilane (Fisher Scientific) for 15 minutes. Upon extensive rinsing, coverslips were dried with air and cured at 100° C. for 1 hour. Next, silanized coverslips were coated with 0.1 mg mL$^{-1}$ rat tail collagen type I (Corning) in 4° C. for 3 hours under shaking conditions. Micropattern designs were modeled in CorelDrawX7 (Corel Corporation) and fabricated into 250 μm thick PDMS stencils (Rogers Corporation) by a laser engraver (Epilog). Stencil design was a circular feature of 5 mm diameter cut into a 13 mm circle. Stencils were then thoroughly rinsed in 70% isopropanol and deionized water, air-dried, and aligned onto the collagen-coated coverslips. The whole substrate was blocked with 0.2% w/v pluronic F-127 (Sigma) diluted in 1×PBS, rinsed with PBS, then with DMEM. Next, 300,000 MCF-7 human breast cancer cells (ATCC) were seeded. After cells adhered, PDMS stencils were peeled off and the glass coverslips with micropatterned cancer cells were briefly rinsed[41].

Fabrication of Hypoxia Device.

The design and toolpaths for the hypoxia microdevice were created using Autodesk Fusion360 (Autodesk, Inc.). The design consists of a base structure to immobilize the coverslip and a cap structure with a diffusion barrier pillar. Subsequently, the design was converted into a g-code, imported into a commercial software (Otherplan, Other Machine Co.), and milled with a computer numerical control machine (Othermill V2, Other Machine Co.). The base and cap structures were milled in DELRIN® and polycarbonate, respectively. Upon mechanical polishing using 1000 grit sandpaper (3 M), microdevices were autoclaved before use. For drug assays, the polycarbonate cap was vapor polished with methylene chloride inside a fume hood to achieve optical transparency[34].

Substrates with micropatterned cells were set into autoclaved microdevices and incubated for specified times. Samples were then fixed in 4% paraformaldehyde (PFA; Electron Microscopy Sciences) for 10 minutes or ice-cold 100% ethanol for immunostaining and LCM, respectively.

COMSOL Multiphysics® Modeling.

The transient diffusion of oxygen in the microdevice was modeled using finite element methods (COMSOL Multiphysics® software, COMSOL Inc.). Passive oxygen diffusion within the media was assumed to be governed by the generic diffusion equation of gas in water[70], with a diffusion coefficient of $3\times10^{-9}$ $m^2$ $s^{-1}$. Boundary conditions were approximated so that the microdevice was impermeable to oxygen and the media surface in direct contact with atmospheric media had a fixed concentration of oxygen corresponding to normoxic levels (0.2 mol m$^{-3}$). Cellular oxygen consumption was assumed to follow Michaelis-Menten kinetics with a logistic function constraining consumption below a critical oxygen level:

$$R_{O_2} = R_{max}\left(\frac{c}{c + k_{MM,O_2}}\right) \cdot \delta(C > C_{cr}) \quad (1)$$

where $R_{max}$ is the maximum oxygen consumption rate of MCF-7 cells adjusted for their average cell volume (0.034 mol s$^{-1}$ m$^{-3}$)[63,70,89], $k_{MM,O2}$ is the Michaelis-Menten constant corresponding to the oxygen concentration where consumption is half maximal, $C_{cr}$ is the critical oxygen concentration below which necrosis is assumed to happen and cells cease oxygen consumption, and $\delta$ is the step-down function accounting for the termination of oxygen consumption[70]. The step-down function was COMSOL's smoothed Heaviside function with a continuous first derivative and no overshoot (flc1hs in COMSOL Multiphysics®). All geometries in the model were defined with an extremely fine mesh in COMSOL Multiphysics®. The model was then solved as a time-dependent study up to 1,440 minutes (time step=1 minute), where the device and the media were assumed to be equilibrated to normoxia at t=0.

Physiological Oxygen Concentration Measurement.

Oxygen levels were measured using fluorophore-based microparticle sensors[40]. Briefly, 2 g of 10-14 μm grade 7 silica gel (Sigma Aldrich) were stirred with 40 mL of 0.1 N NaOH for 30 minutes; then with 10 mL ethanol solutions of 0.5 mM tris(4,7-diphenyl-1,10-phenanthroline) ruthenium (II) dichloride (Thermo Fisher) and 0.5 mM Nile blue chloride (Sigma Aldrich), respectively, for 30 minutes. The solution was then centrifuged for 20 minutes at 1900×g. The pellet was washed and centrifuged with the same settings thrice with deionized water, and once with ethanol. The fluorophore-immobilized silica gel pellet was then dried in a 70° C. oven overnight. Simultaneously, a lid structure that fits the diffusion barrier pillar was milled with polycarbonate and silanized with trichloro(1H, 1H,2H,2H-perfluorooctyle) silane (Sigma Aldrich) overnight. The following day, fluorophore-immobilized silica gel was mixed with PDMS of 1:10 base to curing agent (Sylgard 184 elastomer kit; Dow Corning) at a 1:20 ratio in an AR-100 Thinky mixer (Thinky U.S.A., Inc.). The mixture was then poured onto the microdevice's pillar, covered with the lid, and cured overnight. Upon detaching the lid, the coated cap was imaged in 1×PBS equilibrated with normoxic air and then incubated with micropatterned cells. After 24 hours, fluorescence from the pillar surface was imaged.

Immunostaining.

After 24 hours of hypoxia or normoxia incubation, 4% PFA-fixed samples were permeabilized with 0.1% Triton X-100 (Fisher Scientific), blocked with 4% bovine serum albumin (GE Healthcare Bio-Sciences), incubated in primary and secondary antibody, and mounted with FluoroGel II containing DAPI (Electron Microscopy Sciences) onto glass slides. Primary antibodies used were monoclonal anti-pimonidazole antibody (9.7.11, 1:50) (Hypoxyprobe, Inc.) and anti-Glucose Transporter 1 (Glut-1) antibody (ab15309, 1:200) (Abcam). In the case of pimonidazole staining, cells were incubated with 200 μM pimonidazole 2 hours before fixation. Pimonidazole and Glut-1 were detected with Alexa Fluor fluorescent dye-conjugated secondary antibodies (Life Technologies). A Nikon inverted fluorescent microscope was used to image immunostained samples.

Gene Expression Assay.

Additionally, cells were laser capture microdissected (Arcturus XT Laser Capture Microdissection System) at locations corresponding to the pillar center and pillar edge after 24 hours of hypoxia or normoxia treatment. RNA was extracted from these cells (Arcturus PicoPure RNA Isolation Kit) and the quality was evaluated with a Varioskan LUX multimode microplate reader (Thermo Fisher Scientific). RNA samples were then reverse transcribed into cDNA with a T100™ Thermal Cycler (BIO-RAD) and amplified with the T100 CFX384 Touch Real-Time PCR Detection System (BIO-RAD) to assess expression of selected gene candidates[45,47-50,90-92]. Data were normalized against β-actin, a housekeeping gene that was confirmed to have relatively stable expression regardless of normoxic or hypoxic conditions[93], and an internal sample control (ΔΔCt method). These ΔΔCt values were plotted in log 2 scale and used to assess gene expression control.

Hypoxia-Activated Drug Assays.

Micropatterned cells were pre-conditioned in normoxic conditions (no microdevice) or hypoxic conditions (microdevice) for 12 hours. Next, media was replaced with 50 μM TPZ (Sigma Aldrich), a hypoxia-activated anticancer prodrug, for 24 hours. Cells were rinsed with fresh media and stained for calcein-AM (Sigma Aldrich) and propidium iodide (PI) (Thermo Fisher Scientific) for 30 minutes at room temperature. Cell survival was quantified by the fraction of cells expressing positive calcein signal.

Image Analysis.

Images were analyzed using the ImageJ and MATLAB software. For oxygen measurements, fluorescent intensity from identified sensor microparticles was quantified independently in each fluorophore's corresponding fluorescence channel (Acridine Orange for ruthenium compound and Cy5 for Nile blue chloride). Raw, pixel-by-pixel fluorescence from tris(4,7-diphenyl-1,10-phenanthroline) ruthenium(II) dichloride was divided by those from Nile blue chloride to obtain a ratio of differential quenching in the oxygen-sensitive and -insensitive fluorophores depending on oxygen levels. This data was then binned into concentric circles with fixed step size (13.5 μm) from the measured centroid of each pillar and related to "sensed" oxygen concentration following a conventional Stern-Volmer model[40,73]:

$$\frac{I_{R,O}}{I_R} - 1 = K_{SV}[O_2] \quad (2)$$

where $I_{R,O}$ and $I_R$ are the fluorescence ratio of the two fluorophores in the absence and presence of oxygen, respectively, and $K_{SV}$ is the Stern-Volmer quenching constant. Derived oxygen concentrations for each bin were plotted against pillar radii.

For immunostained samples, the fraction of micropattern area with fluorescence above a pre-defined threshold value was measured. This fraction was also binned into 100 radially evolving concentric circles and plotted against micropattern radii.

For the drug assay, the fraction of calcein positive cells (live cells) within (corresponding to hypoxia-induced cells under the pillar) and outside (corresponding to near-normoxic cells outside the pillar) the 1.5 mm radius was quantified. The fraction of PI positive cells (dead cells) was also quantified. The respective fractions were plotted against micropattern radii, similarly to previous image analyses. All data are plotted using Prism (GraphPad Software, Inc.).

Statistical Analysis.

All data are presented in mean±S.D. Pearson's correlation coefficient (r) was used to depict correlation between readings from the oxygen sensors and the COMSOL simulation, as well as pimonidazole and Glut-1 staining. Statistics for gene expression was generated using Student's t-test. Statistics for drug treatment study was assessed using the one-way ANOVA. In all statistical analysis, p<0.05 was considered significant.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. Siegel, R. L., Miller, K. D. & Jemal, A. Cancer statistics, 2017. *CA. Cancer J Clin.* 67, 7-30 (2017).
2. Tafe, L. J. Molecular mechanisms of therapy resistance in solid tumors: chasing 'moving' targets. *Virchows Arch. Int. J. Pathol.* https://doi.org/10.1007/s00428-017-2101-7 (2017).
3. Muz, B., de la Puente, P., Azab, F. & Azab, A. K. The role of hypoxia in cancer progression, angiogenesis, metastasis, and resistance to therapy. *Hypoxia Auckl. NZ* 3, 83-92 (2015).
4. Balkwill, F. R., Capasso, M. & Hagemann, T. The tumor microenvironment at a glance. *J Cell Sci* 125, 5591-5596 (2012).
5. Hanahan, D. & Weinberg, R. A. Hallmarks of Cancer: The Next Generation. *Cell* 144, 646-674 (2011).
6. Wigerup, C., Påhlman, S. & Bexell, D. Therapeutic targeting of hypoxia and hypoxia-inducible factors in cancer. *Pharmacol. Ther.* 164, 152-169 (2016).
7. Brown, J. M. & Wilson, W. R. Exploiting tumour hypoxia in cancer treatment. *Nat. Rev. Cancer* 4, 437-447 (2004).
8. McKeown, S. R. Defining normoxia, physoxia and hypoxia in tumours—implications for treatment response. *Br. J. Radiol.* 87 (2014).
9. Harris, A. L. Hypoxia—a key regulatory factor in tumour growth. *Nat. Rev. Cancer* 2, 38-47 (2002).
10. Eales, K. L., Hollinshead, K. E. R. & Tennant, D. A. Hypoxia and metabolic adaptation of cancer cells. *Oncogenesis* 5, e190 (2016).
11. Marusyk, A., Almendro, V. & Polyak, K. Intra-tumour heterogeneity: a looking glass for cancer? *Nat. Rev. Cancer* 12, 323-334 (2012).
12. Yamada, K. M. & Cukierman, E. Modeling Tissue Morphogenesis and Cancer in 3D. *Cell* 130, 601-610 (2007).
13. Gerling, M. et al. Real-Time Assessment of Tissue Hypoxia In vivo with Combined Photoacoustics and High-Frequency Ultrasound. *Theranostics* 4, 604-613 (2014).
14. Bauer, N., Liu, L., Aleksandrowicz, E. & Herr, I. Establishment of hypoxia induction in an in vivo animal replacement model for experimental evaluation of pancreatic cancer. *Oncol. Rep.* 32, 153-158 (2014).
15. Mak, I. W., Evaniew, N. & Ghert, M. Lost in translation: animal models and clinical trials in cancer treatment. *Am. J. Transl. Res.* 6, 114-118 (2014).
16. Katt, M. E., Placone, A. L., Wong, A. D., Xu, Z. S. & Searson, P. C. In Vitro Tumor Models: Advantages, Disadvantages, Variables, and Selecting the Right Platform. *Front. Bioeng. Biotechnol.* 4 (2016).
17. Condeelis, J. & Weissleder, R. In vivo Imaging in Cancer. *Cold Spring Harb. Perspect. Biol.* 2 (2010).
18. Wu, D. & Yotnda, P. Induction and Testing of Hypoxia in Cell Culture. *JoVE J. Vis. Exp.* e2899-e2899, https://doi.org/10.3791/2899 (2011).
19. Wang, R., Jin, F. & Zhong, H. A novel experimental hypoxia chamber for cell culture. *Am. J. Cancer Res.* 4, 53-60 (2014).
20. Grimes, D. R., Kelly, C., Bloch, K. & Partridge, M. A method for estimating the oxygen consumption rate in multicellular tumour spheroids. *J. R. Soc. Interface* 11, 20131124 (2014).
21. Thomas, P. C., Raghavan, S. R. & Forry, S. P. Regulating Oxygen Levels in a Microfluidic Device. *Anal. Chem.* 83, 8821-8824 (2011).
22. Sheta, E. A., Trout, H., Gildea, J. J., Harding, M. A. & Theodorescu, D. Cell density mediated pericellular hypoxia leads to induction of HIF-1alpha via nitric oxide and Ras/MAP kinase mediated signaling pathways. *Oncogene* 20, 7624-7634 (2001).
23. Walsh, J. C. et al. The Clinical Importance of Assessing Tumor Hypoxia: Relationship of Tumor Hypoxia to Prognosis and Therapeutic Opportunities. *Antioxid. Redox Signal.* 21, 1516-1554 (2014).
24. Fischbach, C. et al. Engineering tumors with 3D scaffolds. *Nat. Methods* 4, 855-860 (2007).
25. Lorenzo, C. et al. Live cell division dynamics monitoring in 3D large spheroid tumor models using light sheet microscopy. *Cell Div.* 6, 22 (2011).
26. Ivanov, D. P. & Grabowska, A. M. Spheroid arrays for high-throughput single-cell analysis of spatial patterns and biomarker expression in 3D. *Sci. Rep.* 7 (2017).
27. Derda, R. et al. Paper-supported 3D cell culture for tissue-based bioassays. *Proc. Natl. Acad. Sci.* 106, 18457-18462 (2009).
28. Peng, C.-C., Liao, W.-H., Chen, Y.-H., Wu, C.-Y. & Tung, Y.-C. A microfluidic cell culture array with various oxygen tensions. *Lab. Chip* 13, 3239-3245 (2013).
29. Chang, C.-W. et al. A polydimethylsiloxane-polycarbonate hybrid microfluidic device capable of generating perpendicular chemical and oxygen gradients for cell culture studies. *Lab. Chip* 14, 3762-3772 (2014).
30. Brennan, M. D., Rexius-Hall, M. L. & Eddington, D. T. A 3D-Printed Oxygen Control Insert for a 24-Well Plate. *PLOS ONE* 10, e0137631 (2015).
31. Ayuso, J. M. et al. Development and characterization of a microfluidic model of the tumour microenvironment. *Sci. Rep.* 6, srep36086 (2016).
32. Li, Y. et al. A microfluidic chip of multiple-channel array with various oxygen tensions for drug screening. *Microfluid. Nanofluidics* 20, 97 (2016).
33. Rexius-Hall, M. L., Mauleon, G., Malik, A. B., Rehman, J. & Eddington, D. T. Microfluidic platform generates oxygen landscapes for localized hypoxic activation. *Lab. Chip* 14, 4688-4695 (2014).
34. Yen, D. P., Ando, Y. & Shen, K. A cost-effective micromilling platform for rapid prototyping of microdevices. *Technology* 04, 234-239 (2016).

35. Moon, S. I., Monson, L. & Extrand, C. W. Outgassing of Oxygen from Polycarbonate. *ACS Appl. Mater. Interfaces* 1, (1539-1543 (2009).
36. Kim, M.-C., Lam, R. H. W., Thorsen, T. & Asada, H. H. Mathematical analysis of oxygen transfer through polydimethylsiloxane membrane between double layers of cell culture channel and gas chamber in microfluidic oxygenator. *Microfluid. Nanofluidics* 15, 285-296 (2013).
37. Houston, K. S., Weinkauf, D. H. & Stewart, F. F. Gas transport characteristics of plasma treated poly(dimethylsiloxane) and polyphosphazene membrane materials. *J. Membr. Sci.* 205, 103-112 (2002).
38. Hammond, E. M. et al. The Meaning, Measurement and Modification of Hypoxia in the Laboratory and the Clinic. *Clin. Oncol.* 26, 277-288 (2014).
39. Höckel, M. & Vaupel, P. Tumor Hypoxia: Definitions and Current Clinical, Biologic, and Molecular Aspects. *JNCI J. Natl. Cancer Inst.* 93, 266-276 (2001).
40. Acosta, M. A., Ymele-Leki, P., Kostov, Y. V. & Leach, J. B. Fluorescent microparticles for sensing cell microenvironment oxygen levels within 3D scaffolds. *Biomaterials* 30, 3068-3074 (2009).
41. Shen, K. et al. Resolving cancer-stroma interfacial signalling and interventions with micropatterned tumour-stromal assays. *Nat. Commun.* 5, 5662 (2014).
42. Gulliksrud, K., Vestvik, I. K., Galappathi, K., Mathiesen, B. & Rofstad, E. K. Detection of Different Hypoxic Cell Subpopulations in Human Melanoma Xenografts by Pimonidazole Immunohistochemistry. *Radiat. Res.* 170, 638-650 (2008).
43. Ragnum, H. B. et al. The tumour hypoxia marker pimonidazole reflects a transcriptional programme associated with aggressive prostate cancer. *Br. J. Cancer* 112, 382-390 (2015).
44. Deng, D. et al. Crystal structure of the human glucose transporter GLUT1. *Nature* 510, 121-125 (2014).
45. Airley, R. E. et al. GLUT-1 and CAIX as intrinsic markers of hypoxia in carcinoma of the cervix: Relationship to pimonidazole binding. *Int. J. Cancer* 104, 85-91 (2003).
46. Dowsett, M. et al. Assessment of Ki67 in Breast Cancer: Recommendations from the International Ki67 in Breast Cancer Working Group. *JNCI J. Natl. Cancer Inst.* 103, 1656-1664 (2011).
47. Bando, H., Toi, M., Kitada, K. & Koike, M. Genes commonly upregulated by hypoxia in human breast cancer cells MCF-7 and MDA-MB-231. *Biomed. Pharmacother.* 57, 333-340 (2003).
48. Hamdan, F. H. & Zihlif, M. A. Gene expression alterations in chronic hypoxic MCF7 breast cancer cell line. *Genomics* 104, 477-481 (2014).
49. Zhang, L. et al. Hypoxia induces epithelial-mesenchymal transition via activation of SNAI1 by hypoxia-inducible factor-1α in hepatocellular carcinoma. *BMC Cancer* 13, 108 (2013).
50. Azab, A. K. et al. Hypoxia promotes dissemination of multiple myeloma through acquisition of epithelial to mesenchymal transitionlike features. *Blood* 119, 5782-5794 (2012).
51. Johnson, C. A. et al. Phase I trial of tirapazamine in combination with cisplatin in a single dose every 3 weeks in patients with solid tumors. *J. Clin. Oncol.* 15, 773-780 (1997).
52. Zeman, E. M., Brown, J. M., Lemmon, M. J., Hirst, V. K. & Lee, W. W. SR-4233: a new bioreductive agent with high selective toxicity for hypoxic mammalian cells. *Int. J. Radiat. Oncol. Biol. Phys.* 12, 1239-1242 (1986).
53. Lee, C.-I., Huang, C.-M., Huang, W.-H. & Lee, A.-R. Synthesis, Preferentially Hypoxic Apoptosis and Anti-Angiogenic Activity of 3-Amino-1,2,4-Benzotriazine-1,4-Dioxide Bearing Alkyl Linkers with a 3-Amino-1,2,4-Benzotriazine-1-Oxide Moiety. *Anticancer Agents Med. Chem.* 14, 1428-1446 (2014).
54. Wang, Z., Liu, Z., Li, L. & Liang, Q. Investigation into the hypoxia-dependent cytotoxicity of anticancer drugs under oxygen gradient in a microfluidic device. *Microfluid. Nanofluidics* 19, 1271-1279 (2015).
55. Smith, A. Screening for drug discovery: The leading question. *Nature* 418, 453-459 (2002).
56. Hughes, J., Rees, S., Kalindjian, S. & Philpott, K. Principles of early drug discovery. *Br. J. Pharmacol.* 162, 1239-1249 (2011).
57. Rosowski, K. A., Mertz, A. F., Norcross, S., Dufresne, E. R. & Horsley, V. Edges of human embryonic stem cell colonies display distinct mechanical properties and differentiation potential. *Sci. Rep.* 5, 14218 (2015).
58. Yoshida, Y., Takahashi, K., Okita, K., Ichisaka, T. & Yamanaka, S. Hypoxia enhances the generation of induced pluripotent stem cells. *Cell Stem Cell* 5, 237-241 (2009).
59. Castilla, D. M., Liu, Z.-J. & Velazquez, O. C. Oxygen: Implications for Wound Healing. *Adv. Wound Care* 1, 225-230 (2012).
60. Colmone, A. Hypoxic conditioning of immune cells. *Science* 355, 706-706 (2017).
61. Palazón, A., Aragonés, J., Morales-Kastresana, A., Landázuri, M. Ode & Melero, I. Molecular Pathways: Hypoxia Response in Immune Cells Fighting or Promoting Cancer. *Clin. Cancer Res.* 18, 1207-1213 (2012).
62. Charati, S. G. & Stern, S. A. Diffusion of Gases in Silicone Polymers: Molecular Dynamics Simulations. *Macromolecules* 31, 5529-5535 (1998).
63. Wagner, B. A., Venkataraman, S. & Buettner, G. R. The Rate of Oxygen Utilization by Cells. *Free Radic. Biol. Med.* 51, 700-712 (2011).
64. Chen, Z. & Turng, L.-S. A review of current developments in process and quality control for injection molding. *Adv. Polym. Technol.* 24, 165-182 (2005).
65. Oskarsson, T. Extracellular matrix components in breast cancer progression and metastasis. *Breast Edinb. Scotl.* 22(Suppl 2), S66-72 (2013).
66. Harisi, R. & Jeney, A. Extracellular matrix as target for antitumor therapy. *OncoTargets Ther.* 8, 1387-1398 (2015).
67. Zhu, J. & Marchant, R. E. Design properties of hydrogel tissue-engineering scaffolds. *Expert Rev. Med. Devices* 8, 607-626 (2011).
68. Polacheck, W. J. & Chen, C. S. Measuring cell-generated forces: a guide to the available tools. *Nat. Methods* 13, 415-423 (2016).
69. Ma, X. et al. Deterministically patterned biomimetic human iPSC-derived hepatic model via rapid 3D bioprinting. *Proc. Natl. Acad. Sci.* 113, 2206-2211 (2016).
70. Buchwald, P. FEM-based oxygen consumption and cell viability models for avascular pancreatic islets. *Theor. Biol. Med. Model.* 6, 5 (2009).
71. Bassom, A. P., Ilchmann, A. & Voß, H. Oxygen Diffusion in Tissue Preparations with Michaelis-Menten Kinetics. *J. Theor. Biol.* 185, 119-127 (1997).
72. Winer, L. S. P. & Wu, M. Rapid Analysis of Glycolytic and Oxidative Substrate Flux of Cancer Cells in a Microplate. *PLOS ONE* 9, e109916 (2014).

73. Wang, X. & Wolfbeis, S. O. Optical methods for sensing and imaging oxygen: materials, spectroscopies and applications. *Chem. Soc. Rev.* 43, 3666-3761 (2014).

74. Becker, W. Fluorescence lifetime imaging-techniques and applications. *J. Microsc.* 247, 119-136 (2012).

75. Sud, D. & Mycek, M.-A. Calibration and validation of an optical sensor for intracellular oxygen measurements. *J. Biomed. Opt.* 14, 020506-020506-3 (2009).

76. Wang, J. Electrochemical Glucose Biosensors. *Chem. Rev.* 108, 814-825 (2008).

77. Usuba, R. et al. Photonic Lab-on-a-Chip for Rapid Cytokine Detection. *ACS Sens.* 1, 979-986 (2016).

78. Ellis, J. M. & Wolfgang, M. J. A genetically encoded metabolite sensor for malonyl-CoA. *Chem. Biol.* 19, 1333-1339 (2012).

79. Kubon, M. et al. A microsensor system to probe physiological environments and tissue response. In 2010 *IEEE Sensors* 2607-2611, https://doi.org/10.1109/ICSENS.2010.5690200 (2010).

80. Behjati, S. & Tarpey, P. S. What is next generation sequencing? *Arch. Dis. Child. Educ. Pract. Ed.* 98, 236-238 (2013).

81. Brewis, I. A. & Brennan, P. Proteomics technologies for the global identification and quantification of proteins. *Adv. Protein Chem. Struct. Biol.* 80, 1-44 (2010).

82. Semenza, G. L. Targeting HIF-1 for cancer therapy. *Nat. Rev. Cancer* 3, 721-732 (2003).

83. Pang, M.-F. et al. Tissue Stiffness and Hypoxia Modulate the Integrin-Linked Kinase ILK to Control Breast Cancer Stem-like Cells. *Cancer Res.* 76, 5277-5287 (2016).

84. Misra, A., Pandey, C., Sze, S. K. & Thanabalu, T. Hypoxia Activated EGFR Signaling Induces Epithelial to Mesenchymal Transition (EMT). *PLOS ONE* 7, e49766 (2012).

85. Reddy, S. B. & Williamson, S. K. Tirapazamine: a novel agent targeting hypoxic tumor cells. *Expert Opin. Investig. Drugs* 18, 77-87 (2009).

86. Hamann, S. et al. Measurement of Cell Volume Changes by Fluorescence Self-Quenching. *J. Fluoresc.* 12, 139-145 (2002).

87. Iannetti, E. F., Smeitink, J. A. M., Beyrath, J., Willems, P. H. G. M. & Koopman, W. J. H. Multiplexed high-content analysis of mitochondrial morphofunction using live-cell microscopy. *Nat. Protoc.* 11, 1693-1710 (2016).

88. Al-Lazikani, B., Banerji, U. & Workman, P. Combinatorial drug therapy for cancer in the post-genomic era. *Nat. Biotechnol.* 30, 679-692 (2012).

89. Moreno-Flores, S., Benitez, R. & Vivanco, M. dM & Toca-Herrera, J. L. Stress relaxation microscopy: Imaging local stress in cells. *J. Biomech.* 43, 349-354 (2010).

90. DeYoung, M. P., Horak, P., Sofer, A., Sgroi, D. & Ellisen, L. W. Hypoxia regulates TSC1/2-mTOR signaling and tumor suppression through REDD1-mediated 14-3-3 shuttling. *Genes Dev.* 22, 239-251 (2008).

91. Pistollato, F. et al. Interaction of hypoxia-inducible factor-1α and Notch signaling regulates medulloblastoma precursor proliferation and fate. *Stem Cells Dayt. Ohio* 28, 1918-1929 (2010).

92. Jundt, F. et al. Activated Notch1 signaling promotes tumor cell proliferation and survival in Hodgkin and anaplastic large cell lymphoma. *Blood* 99, 3398-3403 (2002).

93. Caradec, J. et al. 'Desperate house genes': the dramatic example of hypoxia. *Br. J. Cancer* 102, 1037-1043 (2010).

What is claimed is:

1. A device for inducing an oxygen concentration gradient, the device comprising:
    a first component that is a diffusion barrier having a first space-defining surface;
    a second component having a second space-defining surface, the first component being positioned proximate to the second component such that the first space-defining surface and the second space-defining surface define a confined space;
    a layer of living cells disposed over the second space-defining surface; and
    an aqueous solution having dissolved oxygen therein that fills the confined space, wherein the first space-defining surface and the second space-defining surface are sufficiently close that passive oxygen diffusion in the confined space is insufficient to replenish oxygen consumed by cells thereby establishing an oxygen gradient in the confined space wherein the first component includes a cap structure with a central oxygen barrier pillar and three spatial reference pillars that are longer than the central oxygen barrier pillar thereby defining a gap distance between the layer of living cells and the central oxygen barrier pillar.

2. The device of claim 1 wherein the first space-defining surface and the second space-defining surface are separated by a gap distance from about 30 μm to about 1000 μm.

3. The device of claim 1 wherein the first space-defining surface and the second space-defining surface are separated by a gap distance from about 50 μm to about 500 μm.

4. The device of claim 1 wherein the first space-defining surface and the second space-defining surface are substantially flat in the vicinity of the confined space.

5. The device of claim 1 wherein the first space-defining surface is curved.

6. The device of claim 1 wherein the first space-defining surface is cone-shaped.

7. The device of claim 1 wherein the confined space is open along a periphery.

8. The device of claim 7 wherein the first space-defining surface is circular.

9. The device of claim 1 wherein the layer of living cells has a smaller spatial dimension that the first space-defining surface.

10. The device of claim 1 further comprising an extracellular component associated with the layer of living cells, the extracellular component having tunable mechanical properties and/or biochemical properties.

11. The device of claim 1 wherein the layer of living cells includes cancer cells or stem cells.

12. The device of claim 1 wherein the layer of living cells includes cells selected from the group consisting of cancer cells, stem cells, cardiomyocytes, neurons, hepatocytes, pancreatic cells, fibroblasts, immune cells, epithelial cells, endothelial cells, and combinations thereof.

13. The device of claim 1 further comprising at least one additional layer of living cells disposed over the second space-defining surface such that a 3-dimension network of cells is created.

14. The device of claim 1 wherein the confined space is a longitudinal channel having a closed end and an open end.

15. The device of claim 13 wherein the second component includes a base structure and a glass plate held by the base structure, the plurality of living cells being disposed over the glass plate.

16. A device for inducing an oxygen concentration gradient, the device comprising:

a first component that is an oxygen diffusion barrier having a first space-defining surface; and
a second component that is an oxygen diffusion barrier, the second component having a second space-defining surface, the first component being positioned proximate to the second component such that the first space-defining surface and the second space-defining surface define a confined space, the confined space defining a gap distance that is sufficiently small to induce the oxygen concentration gradient when a layer of living cells in aqueous medium is disposed in the confined space wherein the first component includes a cap structure with a central oxygen barrier pillar and spatial reference pillars that are longer than the central oxygen barrier pillar thereby defining a gap size between the layer of living cells and the central oxygen barrier pillar.

17. The device of claim 16 wherein the gap distance is from about 30 μm to about 1000 μm.

18. The device of claim 16 wherein the gap distance is from about 50 μm to about 500 μm.

19. The device of claim 16 wherein the first space-defining surface and the second space-defining surface are substantially flat in the vicinity of the confined space.

20. The device of claim 16 wherein the confined space is a longitudinal channel having a closed end and an open end.

21. The device of claim 16 wherein the second component includes a base structure and a glass plate held by the base structure, the plurality of living cells being disposed over the glass plate.

22. An integrated system comprising
a device for inducing an oxygen concentration gradient, the device defining a spatially confined region that induces an oxygen gradient when a layer of living cells is disposed within the spatially confined region, the device comprising:
a first component that is a diffusion barrier having a first space-defining surface;
a second component having a second space-defining surface, the first component being positioned proximate to the second component such that the first space-defining surface and the second space-defining surface define a confined space, wherein the first component includes a cap structure with a central oxygen barrier pillar and spatial reference pillars that are longer than the central oxygen barrier pillar thereby defining a gap size between the layer of living cells and the central oxygen barrier pillar; and
a microfluidic channel, the microfluidic channel providing materials to the layer of living cells.

23. The integrated system of claim 22 wherein the device for inducing an oxygen concentration gradient comprises:
the layer of living cells disposed over the second space-defining surface; and
an aqueous solution having dissolved oxygen therein that fills the confined space, wherein the first space-defining surface and the second space-defining surface are sufficiently close that passive oxygen diffusion in the confined space is insufficient to replenish oxygen consumed by cells thereby establishing the oxygen gradient in the confined space.

24. The integrated system of claim 23 wherein the microfluidic channel includes porous membrane regions in fluid communication with the confined space.

25. The integrated system of claim 24 wherein drugs and/or therapeutic cells are delivered to layer of living cells via microfluidic channel.

26. The integrated system of claim 24 wherein endothelial cells are delivered to layer of living cells via microfluidic channel.

* * * * *